(12) United States Patent
Mitra

(10) Patent No.: US 6,541,272 B1
(45) Date of Patent: Apr. 1, 2003

(54) PULSE INTRODUCTION MEMBRANE EXTRACTION APPARATUS AND METHOD FOR SEPARATING AND ANALYZING AT LEAST ONE COMPONENT IN A FLUID CONTAMINATED WITH THE AT LEAST ONE COMPONENT

(75) Inventor: Somenath Mitra, Bridgewater, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 09/224,658

(22) Filed: Dec. 31, 1998

(51) Int. Cl.$^7$ .............................................. G01N 1/18
(52) U.S. Cl. ....................... 436/178; 436/161; 436/164; 436/180; 422/63; 422/70; 422/82.05; 422/100; 422/101; 422/103; 73/23.35; 73/61.55; 73/61.59; 73/863.24; 96/105; 95/89; 210/96.2; 210/198.2; 210/500.23; 210/650; 210/656
(58) Field of Search ................................. 210/143, 175, 210/259, 500.23, 511, 634, 650, 806; 436/164, 171, 178, 180; 422/68.1, 69, 70, 101, 256; 73/863.23, 863.24, 864.34

(56) References Cited

U.S. PATENT DOCUMENTS 4,913,821 A * 4/1990 Melcher et al. ............. 436/178
5,160,625 A * 11/1992 Jonsson et al. ........ 210/500.23
5,229,300 A * 7/1993 Yalvac et al. ................ 436/178
5,435,169 A * 7/1995 Mitra
5,492,838 A * 2/1996 Pawliszyn .................... 436/178
5,637,224 A * 6/1997 Sirkar et al. ........... 210/500.23

OTHER PUBLICATIONS

Bauer et al., *Anal. Chem.* 66:4422–4431 (1994).
Mitra et al., *Analytical Letters.* 31:367–379 (1998).
Mitra et al., *J Micro Column Separation.* 8:21–27 (1996).
Mitra et al., *J Chromatography A.* 727:111–118 (1996).
Tsai et al., *Anal. Chem.* 63:2460–2465 (1991).
Xu et al., *J Chromatography A.* 688:171–180 (1994).

* cited by examiner

Primary Examiner—Joseph W. Drodge
(74) Attorney, Agent, or Firm—Klauber & Jackson

(57) ABSTRACT

An apparatus and method for separating and analyzing a component of a fluid sample that is considered to be a contaminant, and particularly, that is or may be an organic material. The invention is predicated on the introduction of the sample fluid in a pulsed manner via a first carrier fluid into a feed chamber. A membrane is located between the feed chamber and an exit chamber, and in fluid registry therewith. When the sample enters the feed chamber, the component to be separated and analyzed can permeate the membrane, and thus passes through the membrane to the exit chamber, and then enters a second carrier fluid which carries it to a detector for analysis. The detector may be a gas chromatograph (GC), mass spectrometer (MS) or the like.

48 Claims, 6 Drawing Sheets

PULSE INTRODUCTION MEMBRANE EXTRACTION APPARATUS AND METHOD FOR SEPARATING AND ANALYZING AT LEAST ONE COMPONENT IN A FLUID CONTAMINATED WITH THE AT LEAST ONE COMPONENT

FIELD OF THE INVENTION

The present invention relates to an apparatus for separation of at least one component from a fluid sample, and then analysis of the at least one component. More particularly, the present invention relates to an apparatus and method for separating and analyzing the quantities of organics, such as volatile organic compounds (VOCs) in a fluid sample such as ground water, drinking water or waste water.

BACKGROUND OF THE INVENTION

In recent years, there has been an increased awareness of the potential contamination of water with organics, which include, but are not limited to nonvolatile organic compounds, alcohols and polymers, and volatile organic compounds (VOCs) such as benzene, toluene, xylene, perchloroethylene, and trichloroethylene. Many of these contaminants in groundwater supplies have originated from the excessive and widespread use of chlorinated hydrocarbons as degreasers, leaks from underground storage tanks, leachate from municipal and industrial landfill sites, or releases in industrial effluent streams.

Methods to separate these contaminants have been developed. One such method, the purge and trap method, is a dynamic head space procedure carried out by purging the VOCs from the fluid sample with the help of an inert fluid, such as $N_2$. The purged VOCs are then trapped in a material to which the VOCs reversibly adsorb. After a predetermined period of time, the VOCs are released from the trap in a concentrated form, and injected into a detector, such as a gas chromatograph or a gas chromatograph coupled to a mass spectrometer. However, this method possesses inherent limitations. In particular, cryogenic trapping of the organic contaminant is required prior to analytical analysis of the contaminate. Cryogenic trapping can result in freezing of moisture in the trap, and a decrease of the efficiency of the apparatus. Furthermore, cold spots in the plumbing of the apparatus also results in carryover problems and memory effects. Consequently, blanks must be run between fluid samples.

Another method used is liquid-liquid extraction. In this method, an organic solvent in which the organic is very soluble, is mixed with the fluid having the VOC contaminant. During this mixing, the organic becomes solubilized in the organic solvent, and thus is removed from the fluid. However, this method also contains inherent limitations. Initially, it involves the use organic solvent. Such solvents are themselves hazardous waste, which are very expensive to dispose of after use. Another potential problem with this method involves replacement costs for replacing solvent containing solubilized organics, which is discarded.

Membrane extraction has also been used to remove and measure a contaminant from a fluid sample. In this method, a fluid sample containing an organic is continuously contacted with a membrane having chemical and physical properties that permits the organic to diffuse into and across the membrane, but prevents the fluid sample from diffusing across and into the membrane. As a result, the organic is separated from the fluid. Hence, this method does not require any solvents or solid phases. However, this method as generally used heretofore, possesses inherent limitations. Initially, such methods are generally used in continuous monitoring, and require large amounts of fluid sample. Hence, it is very difficult with presently known membrane extraction systems to remove the organic from a small amount of fluid sample. Furthermore, in order to obtain accurate measurements of the organics in the fluid, an equilibrium must be established in the membrane such that the amount of organic leaving the membrane and the amount entering the membrane are in a steady state. Until this steady state is achieved, measurements of the amount of organic in the fluid will be inaccurate. Moreover, in order to reach this steady state, the fluid sample must flow continuously through the feed chamber, which requires large amounts of fluid sample.

Still another drawback to this method is the lag time involved in obtaining accurate measurements. This lag time is the result of the need to equilibrate the membrane to the concentration of organics in the solution, as explained above, and the necessity of the organics to diffuse through a boundary layer of fluid formed on the surface of the membrane prior to diffusing through the membrane itself.

Accordingly, what is needed is an apparatus and method that permit separation and analysis of organics in a discreet sample of fluid, such as water, having a small volume, e.g., about 1 $\mu$l to about 1 ml, or a moderate volume, e.g. about 1 ml to about 10 ml.

What is also needed is an apparatus or method of separating and analyzing organics in a discreet fluid sample that is not dependent upon equilibration of a membrane, i.e., the reaching of a steady state of component traversing the membrane. As a result, samples of fluid with vastly different concentrations of organics can be analyzed quickly and accurately.

The citation of any reference herein should not be construed as an admission that such reference is available as "Prior Art" to the instant application.

SUMMARY OF THE INVENTION

There are provided, in accordance with the invention, a new and useful apparatus and method for separating and analyzing at least one component of a fluid sample that do not possess the shortcomings of apparatuses and methods described above. Hence, the present invention is not dependent upon equilibration of the permeation of the component through a membrane, and can analyze a fluid sample having a discreet volume, even if the volume is small (about 1 $\mu$l to about 1 ml) or medium (about 1 ml to about 10 ml) in size. As a result, the present invention offers the advantages of permitting analysis of discreet volumes of fluid samples accurately and quickly.

Broadly, the present invention extends to an apparatus for separating and analyzing at least one component of a fluid sample, the apparatus comprising a feed chamber having an entrance and an exit, a first flow means for flowing a first carrier fluid through the feed chamber, a means for injecting a pulse of fluid sample into the flow of the first carrier fluid such that the pulse of fluid sample enters the feed chamber, an exit chamber downstream from the feed chamber, at least one membrane through which the at least one component can selectively permeate, wherein the at least one membrane is located between the feed chamber and the exit chamber, and is fluid registry with the feed chamber and the exit second chamber, a detector in fluid communication with the exit chamber, wherein the detector analyzes the at least component that passes through the membrane and enters the exit chamber, and a second flow means for flowing the at least one component which passes through the at least one membrane and enters the exit chamber, to the detector.

Furthermore, the present invention extends to an apparatus for separating and analyzing at least one component of a fluid sample as described above, wherein the fluid sample comprises an aqueous solution, the at least one component comprises an organic, and the first carrier comprises a water, water with salt or other additives, organic solvents, nitrogen, carbon dioxide, argon, neon, or a combination thereof.

Numerous means are presently available to the skilled artisan to form the first flow means of the invention. A particular means having applications herein comprises a first reservoir which holds the first carrier fluid upstream from the feed chamber, and a pump connected to the first reservoir and in fluid communication therewith. The pump pumps the first carrier fluid from the first reservoir, through the entrance, and then through the exit of the feed chamber. Thus, a flow of the first carrier fluid through the feed chamber is created. Other means of forming such a flow include placing the first carrier fluid in the first reservoir under pressure, and locating a valve downstream from the first reservoir and upstream of the entrance of the feed chamber, wherein the valve is in fluid communication with the first reservoir and the feed chamber. When the valve is opened, the pressure forces the first carrier fluid from the first reservoir and through the feed chamber. Still another means comprises locating a drawing means, such as a vacuum pump in fluid communication with the exit of the feed chamber. When the vacuum is activated, it will draw the first carrier fluid from the first reservoir, and through the feed chamber.

In addition, the present invention extends to the apparatus for separating and analyzing at least one component of a fluid sample as described above, wherein the means for injecting the pulse of fluid sample into the feed chamber comprises a multi-port valve upstream from the feed chamber and downstream from the first reservoir, wherein the multi-port valve is in fluid communication with the first reservoir and the feed chamber, and comprises a first port through which the pulse of fluid sample is injected into the flow of the first carrier fluid. Optionally, a sample loop can be fixed to the multi-port valve. This loop allows one to vary the volume of the pulse of fluid sample injected into the apparatus. Furthermore, such an injection can be made with a syringe in fluid communication with the multi-port valve, or via a reservoir holding the fluid sample, which is in fluid communication with the multi-port valve.

Optionally, the apparatus of the invention can further comprise an a means for flowing a substantially inert purge fluid into the feed chamber after the pulse of fluid sample has passed through the feed chamber. This purge fluid disrupts the fluid layer which develops over the membrane in the fluid chamber, and thus decreases the response time of the instrument. Furthermore, the purge fluid purges any component of the fluid sample that is within the membrane but has not completely passed through the membrane. Hence, these components are purged from the membrane and enter the exit chamber, thus increasing the accuracy of the separation and analysis of the apparatus. Numerous means of flowing the purge fluid into the feed chamber are readily available to one of ordinary skill in the art. A particular means comprises a switching valve located upstream from the multi-port valve and downstream from the first reservoir, and in fluid communication with the first reservoir and the multi-port valve, and a second reservoir for holding the substantially inert purge fluid in fluid communication with the switching valve. The switching valve can be readily manipulated to prevent the first carrier fluid from flowing into the feed chamber after the fluid sample has passed through the feed chamber, and to permit the purge fluid to enter the feed chamber. Also, numerous fluids can serve as the purge fluid. In a particular embodiment, wherein the fluid sample comprises an aqueous solution and the at least one component comprises an organic, the substantially inert purge fluid comprises $N_2$, $CO_2$, neon or helium.

Furthermore, as explained infra, the at least one membrane can be symmetrical or asymmetrical in structure, depending upon the application. In a particular embodiment, the at least one membrane comprises at least one hollow fiber having a bore and an outer surface, and the at least one hollow fiber is contained within a shell, such that the bore defines the feed chamber, and the shell and the outer surface of the hollow fiber define the exit chamber. Furthermore, in a preferred embodiment, the bore of the at least one hollow fiber membrane has a diameter of about 0.305, and the at least one hollow fiber has an outer diameter of 0.635 mm.

Furthermore, the at least one fiber of the invention can be comprised of nonporous hydrophobic material, such as polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, or polyethers, to name only a few. In a particular embodiment, the at least one membrane is comprised of polydimethylsiloxane.

In addition, the at least one membrane of the apparatus can be a membrane composite, comprising a porous membrane having a first and second surface, and a nonporous hydrophobic membrane permanently disposed on the second surface of the porous membrane, such that the first surface of the porous membrane is in fluid registry with the exit chamber, and the nonporous hydrophobic membrane is in fluid registry with the feed chamber. Any of the materials described above for use in the at least one membrane of the invention have applications in the nonporous hydrophobic membrane of the membrane composite. Further, examples of materials which can be used in the porous membrane include, but are not limited to, polypropylene, polyethylene, polytrimethylpentene, polytetrafluoroethylene, polyvinylidene difluoride, or polysulfone, and can have pores ranging in size from about 6 to about 500 Å.

Furthermore, in an embodiment of the invention, a membrane module is used which comprises a plurality of membranes housed within the shell. Hence, the surface area of the at least one membrane can be increased, which increases the efficiency of the present invention.

In addition, an apparatus for separating and analyzing at least one component of a fluid sample of the invention can further comprise an injection means for injecting the at least one component which passes through the membrane and enters the exit chamber, into the detector, wherein the injection means is located downstream from the exit chamber, and upstream from the detector, and in fluid communication with the exit chamber and the detector. An example of an injecting means having applications herein comprises a multi-port valve. Another injection means having applications herein comprises a trap means comprising a column having a first end in fluid communication with the exit chamber and a second end in fluid communication with the detector, wherein the column is packed with a packing material to which the at least one component can reversibly adsorb, and a releasing means which desorbs the at least one component from the packing material. As a result, the at least one component which passes through the membrane and enters the exit chamber, is flowed via a second flow means, which is described infra, from the exit chamber to the trap means. When released from the trap means, the at least one component then flows to the detector via the second carrier fluid.

Numerous materials, such as "TEFLON", polypropylene, stainless steel or glass, can be used to form the column of the trap means. Furthermore, numerous packing materials can be used in the column. In a particular example, wherein the at least one component is an organic, the packing material comprises "TANEX", silica gel, or a carbon based sorbent like charcoal, "CARBOTRAP C" (Supelco, Inc., Supelco, Pa.), "CARBOSIEVE", or a combination thereof. In a particular embodiment of the invention, wherein the at least one component is an organic, the column comprises a length of 15 cm, an outer diameter of 0.53 mm, is comprised of stainless steel, and is packed with "CARBOTRAP C".

Moreover, in this embodiment, the releasing means comprises a means for heating the packing material such that the organics can desorb from the packing material, and then flow into the detector via the second carrier fluid, described infra. A particular heating means having applications with a stainless steel column, comprises a power supply electrically connected to the column, such that an electric current is applied to the column, and the column undergoes resistive heating. As a result of this resistive heating, the packing material is heated and the at least one component can desorb from the packing material, and flow into the detector via the second carrier fluid.

The present invention further extends to an apparatus for separating and analyzing at least one component of a fluid sample, as described above, wherein the detector comprises a high performance liquid chromatograph, a gas chromatograph coupled to a mass spectrometer, a capillary electrophoresis instrument, a mass spectrometer, a total organic carbon analyzer, or an infra red (IR), ultraviolet (UV), Raman or fluorescence spectrometer, to name only a few.

Furthermore, as mentioned above, the present invention extends to an apparatus for separating and analyzing at least one component of a fluid sample, further comprising a second flow means for flowing the at least one component which passes through the at least one membrane, from the exit chamber, optionally to the injection, and then to the detector. In a particular embodiment of the invention, the second flow means comprises a third reservoir holding the second carrier fluid, wherein the second reservoir is in fluid communication with the exit chamber, such that the second carrier fluid flows from the second reservoir through the exit chamber, optionally to the injection means, and then to the detector. Examples of the second carrier fluid having applications herein include, but certainly are not limited to, nitrogen, hydrogen or helium.

Furthermore, the present invention extends to a process for separating and analyzing at least one component of a fluid sample, practiced with an apparatus comprising a feed chamber having an entrance and an exit, a first flow means for flowing a first carrier fluid through the feed chamber, means for injecting a pulse of fluid sample into the flow first carrier fluid such that the pulse of fluid sample enters the feed chamber, an exit chamber downstream from the feed chamber, at least one membrane through which the at least one component can selectively permeate there through, wherein the at least one membrane is located between the feed chamber and the exit chamber, and is fluid registry with the feed chamber and the exit second chamber, a detector in fluid communication with the exit chamber, wherein the detector analyzes the at least component that passes through the membrane and enters the exit chamber, and a second flow means for flowing the at least one component which passes through the at least one membrane and enters the exit chamber, to the detector. The process comprises the steps of flowing the first carrier fluid through the feed chamber, injecting the pulse of fluid sample into the first carrier so that the pulse of fluid sample enters the feed chamber, and detecting the at least one component which passes through the at least one membrane and enters the exit chamber.

Naturally, the at least one membrane of the process can be symmetrical of asymmetrical in structure. In a particular embodiment, the at least one membrane comprises at least one hollow fiber having a bore and an outer surface, and the at least one fiber is contained within a shell, such that the bore defines the feed chamber, and the shell and the outer surface of the at least one hollow fiber define the exit chamber. The hollow fiber membrane of the invention can have numerous dimensions, depending upon the application. In a particular embodiment the at least one hollow fiber has an inner, or bore diameter of 0.305 mm and an outer diameter of 0.635 mm.

Furthermore, in a particular embodiment of the process, the at least one membrane is comprised of a nonporous hydrophobic material. Numerous nonporous hydrophobic materials such as polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, or polyethers, to name only a few, have applications in the invention. In a preferred embodiment of the invention, the at least one membrane is comprised of polydimethylsiloxane (silicone rubber).

Further, the at least one membrane can also be a membrane composite, comprising a porous membrane having a first and second surface, and a nonporous hydrophobic membrane permanently disposed on the second surface of the porous membrane, such that the first surface of the porous membrane is in fluid registry with the feed chamber, and the nonporous hydrophobic membrane is in fluid registry with the exit chamber. Numerous porous materials can be used in the porous membrane of the membrane composite. Particular examples of such materials include polypropylene, polyethylene, polytrimethylpentene, polytetrafluoroethylene, polyvinylidene difluoride, or polysulfone, to name only a few. Also, the pores of the porous membrane can vary in size, from about 6 to about 500 Å, depending upon the particular application. One of ordinary skill in the art is readily able to determine the particular size pores needed for a particular application. Furthermore, the nonporous hydrophobic membrane can be comprises of any of the nonporous hydrophobic materials discussed above. In a preferred embodiment of the membrane composite, the porous membrane comprises polypropylene, and the nonporous hydrophobic membrane comprises polydimethylsiloxane (silicone).

The present invention further extends to a process for separating and analyzing at least one component of a fluid sample as described above, wherein the step of flowing the first carrier fluid through the feed chamber comprises providing a first reservoir which holds the first carrier fluid upstream from the feed chamber, and providing a pump in fluid communication with the first reservoir, such that the first carrier fluid is pumped through the feed chamber.

Various fluids have applications as the first carrier fluid the invention. Particular examples include water, water with salt or other additives, organic solvents, nitrogen, carbon dioxide, argon, neon, or a combination thereof.

In addition, the present invention extends to a process for separating and analyzing at least one component of a fluid sample, wherein the step of injecting the pulse of fluid sample into the feed chamber comprises a multi-port valve upstream from the feed chamber and downstream from the first reservoir. The multi-port valve is in fluid communication with the first reservoir and the feed chamber, and comprises a first port through which the pulse of fluid sample is injected into the flow of the first carrier fluid. Hence, as the first carrier fluid flows from the first reservoir into the feed chamber, the pulse of fluid sample is carried into the feed chamber, where the at least one component is separated from the fluid sample.

Furthermore, the present invention extends to a process for separating and analyzing at least one component of a fluid sample, comprising the steps of flowing the first carrier fluid through the feed chamber, injecting the pulse of fluid sample into the first carrier so that the pulse of fluid sample enters the feed chamber, flowing a substantially inert purge fluid into the feed chamber after the pulse of fluid sample has passed through the feed chamber, and detecting the at least one component which passes through the at least one membrane and enters the exit chamber. In a particular embodiment of the invention, the step of flowing the substantially inert purge fluid into the feed chamber comprises providing a switching valve upstream from the multi-port valve and downstream from the first reservoir, and in fluid communication with the first reservoir and the multi-port valve, and providing a second reservoir for holding the substantially inert purge fluid in fluid communication with the switching valve. This step of the process also comprises operating the switching valve such that the first carrier fluid is prevented from entering the feed chamber after the pulse of fluid sample has passed through the feed chamber, and the substantially inert purge fluid is permitted to flow from the second reservoir into the feed chamber after the pulse of fluid sample has passed through the feed chamber. When in the feed chamber, the purge fluid disrupts the boundary layer which forms on the surface of the at least one membrane, and purges any component in the membrane. Hence, the components in the at least one membrane pass through and enter the exit chamber, resulting in increased accuracy and decreased lag time for the present invention. Numerous fluids can be used as a substantially inert purge fluid. In a particular embodiment, wherein the fluid sample comprises an aqueous solution, and the at least one component comprises an organic, the purge fluid comprises $N_2$, $CO_2$, neon or helium.

Furthermore, the present invention extends to a process for flowing a substantially inert purge fluid into the feed chamber as described above, further comprising the step of injecting the at least one component which passes through the membrane and enters the exit chamber, into the detector. In a particular embodiment, wherein the at least one component comprises an organic, the injecting step comprises the steps of providing a trap means comprising a column having a first end in fluid communication with the exit chamber, and a second end in fluid communication with the detector, wherein the column is packed with a packing material to which the organics can reversibly adsorb. The injection step also comprises providing a releasing means for releasing the at least one component trapped in the trap means, so that the second carrier can flow the released at least one component into the detector. The column of the trap means can be made of any material that does not chemically react with the packing material, the at least one component, and the second carrier fluid. Examples of such materials include, but are not limited to, stainless steel, "TEFLON", polypropylene, or glass. Furthermore, when the at least one component comprises an organic, the packing material is comprised of "TANEX", silica gel or a carbon based sorbent such as charcoal, "CARBOTRAP C" (Supelco, Inc., Supelco, Pa.), "CARBOSIEVE", or a combination thereof. In a particular embodiment the column of the trap means comprises a length of about 15 cm, an outer diameter of about 0.53 mm, is comprised of stainless steel, and is packed with "CARBOTRAP C".

Furthermore, numerous releasing means, i.e., means for heating the packing material such that the organic desorbs from the packing material, have applications herein and are readily available to the skilled artisan. One such heating means comprises a flame place under the column, such that the flame heats the column, which in turn heats the packing material. Another means for heating the column comprises bombarding the column with electromagnetic radiation, such as a microwave, or a laser, which the column can absorb. Such absorption will heat the column and in turn, heat the packing material. Still another means of heating the packing material, wherein the column is made of a material that conducts an electric current, involves conducting an electric current through the column. Hence, in this embodiment of the invention, the releasing means comprises a power supply electrically connected to the column, such that an electric current is applied to the column, and the column undergoes resistive heating which, in turn, heats the packing material.

Naturally the detectors having applications in an apparatus of the invention, such as a gas chromatograph, a high performance liquid chromatograph, a gas chromatograph coupled to a mass spectrometer, a capillary electrophoresis instrument, a mass spectrometer, a total organic carbon analyzer, or an infra red (IR), ultraviolet (UV), Raman or fluorescence spectrometer.

Also, the present invention extends to a process for separating and analyzing at least one component of a sample fluid as described above wherein the step of detecting the at least one component which passes through the at least one membrane comprises flowing a second carrier fluid through the exit chamber, and to the detector. The second carrier fluid carries the at least one component from the exit chamber to the detector for analysis. The step of flowing the second carrier through the exit chamber comprises providing a third reservoir which hold the second carrier fluid under pressure. The third reservoir is in fluid communication with a valve, which is in fluid communication with the exit chamber, so that the valve is downstream of the third reservoir and upstream of the exit chamber. When the valve is opened, the pressure of the second carrier fluid in the third reservoir causes the second carrier fluid to flow from the third reservoir, through the exit chamber, through an injection means, if present, and ultimately to the detector. Numerous fluids can be used as the second carrier fluid in the process of the invention. Particular examples include nitrogen, hydrogen or helium.

In another embodiment, the present invention extends to an apparatus for separating and analyzing at least one component of a fluid sample, wherein the apparatus comprises a feed chamber having an entrance and exit, a first flow means for flowing a first carrier fluid through the feed chamber, means for injecting a pulse of fluid sample into the flow of the first carrier fluid such that the pulse of fluid sample enters the feed chamber, and an exit chamber downstream from the feed chamber. This embodiment also comprises at least one membrane through which the at least one component can selectively permeate, wherein the at least one membrane is located between the feed chamber and the exit chamber, and is fluid registry with the feed chamber and the exit chamber. Furthermore, this embodiment of the apparatus of the invention comprises a means for flowing a substantially inert purge fluid into the feed chamber after the pulse of fluid sample has passed through the feed chamber, a trap means located downstream from the exit chamber and in fluid communication therewith, wherein the at least one component that permeates through the at least one membrane can be trapped. In addition, this embodiment of the invention comprises a releasing means connected to the trap means, wherein the releasing means releases the at least one component trapped in the trap means. This embodiment of apparatus of the invention also comprises a detector in fluid communication with the trap means, wherein the detector analyzes the at least component released from the trap means, and a second flow means for creating a flow of the at least one component from the exit chamber to the trap means, and then from the trap means to the detector when the at least one component is released from the trap means by the releasing means. In a particular embodiment, the pulse of fluid sample has a discreet volume ranging from 1 $\mu$l to, and including 10 ml.

Furthermore, the present invention extends to an apparatus for separating and analyzing at least one component of a fluid sample as described above, wherein the first flow means comprises a first reservoir for holding the first carrier fluid, which is upstream from the feed chamber, and is in fluid communication therewith. Furthermore, a pump, such as peristaltic pump, is in fluid communication with the first reservoir and the feed chamber. Hence, the first fluid carrier is pumped from the first reservoir and into and through the feed chamber. Examples of pumps having applications herein include a peristaltic pump, a mechanical pump or a gear pump, to name only a few. Other means of creating the first flow include placing the first carrier fluid in the reservoir under a pressure and providing a valve located downstream from the first reservoir and upstream from the feed chamber. When the valve is opened, the pressure of the first carrier in the first reservoir will cause the first carrier to exit the first reservoir and flow to the feed chamber. Another means for creating such a flow is to provide a vacuum means, such as with a vacuum pump in fluid communication with the exit of the feed chamber. When, the vacuum means is operating, it will draw the first carrier fluid from the first reservoir and through the feed chamber. Examples of fluids having applications as the first carrier fluid herein include water, water with salt or other additives, organic solvents, or a gas such as nitrogen, carbon dioxide, argon, neon, or a combination thereof.

The present invention further extends to an apparatus for separating and analyzing at least one component of a fluid sample, as set forth above, wherein the means of injecting the pulse of fluid sample into the flow the first carrier fluid comprises a multi-port valve upstream from the feed chamber and downstream from the first reservoir. The multi-port valve is in fluid communication with the first reservoir and the feed chamber, and comprises a port through which the pulse of fluid sample is injected into the flow of the carrier fluid. Optionally, the pulse of fluid sample can originate from a reservoir containing the fluid sample, which is in fluid communication with the multi-port valve.

Alternatively, a pulse of fluid sample having a specific volume can be injected into the multi-port valve with a syringe. In a particular embodiment of the invention, the first carrier fluid is a liquid, and the substantially inert purge fluid comprises a gas. Examples of organics which can be separated from a fluid sample and measured with the apparatus of the invention include benzene, toluene, xylene, perchloroethylene, and trichloroethylene, to name only a few.

Moreover, as explained above, an apparatus of the invention comprises a means for flowing a substantially inert purge fluid into the feed chamber after the pulse of fluid sample has passed through the feed chamber. In a particular embodiment of the invention, wherein a multi-port valve is downstream from the first reservoir and upstream from the feed chamber, the means for flowing the substantially inert purge fluid into the feed chamber after the pulse of fluid sample has passed through the feed chamber comprises a second reservoir for holding the substantially inert purge fluid, which is in fluid communication with the switching valve, and a means for operating the switching valve. The switching valve is located downstream from the first reservoir and upstream from the exit chamber, and in fluid communication with the first reservoir and the exit chamber. When switching valve is operated, the first carrier fluid is prevented from entering the feed chamber after the pulse of fluid sample has passed through the feed chamber, and the substantially inert purge fluid is permitted to flow from the second reservoir into the feed chamber. Hence, a flow of the substantially inert purge fluid is formed which flows into the feed chamber, and may substitute for the flow of the first carrier fluid entering the feed chamber after the pulse of fluid sample has passed through the feed chamber. Numerous means for operating the switching valve in the manner described above are readily apparent to the skilled artisan. A particular means comprises a microprocessor which is in communication with the valve. Alternatively, the switching valve can be operated manually. Examples of a substantially inert purge fluid having applications herein include, but are not limited to, nitrogen, carbon dioxide, neon, or helium.

Also, numerous means for creating a flow of the second carrier fluid as described above are readily available to the skilled artisan, and have applications herein. A particular example comprises a third reservoir for holding the second carrier fluid under pressure, wherein the third reservoir is in fluid communication with the exit chamber, and a valve is located downstream from the third reservoir and upstream of the exit chamber. When the valve is opened, the pressure causes the second carrier fluid to flow from the third reservoir, through the exit chamber, the trap means, and ultimately to the detector, which in turn flows the at least one component which passes through the at least one membrane to the trap means and ultimately to the detector. However, when the valve is closed, the flow of the second carrier fluid as described above is not formed. Examples of fluids having applications as the second carrier fluid include nitrogen, hydrogen, or helium.

Moreover, the present invention extends to an apparatus for separating and analyzing at least one component of a fluid sample as described above, wherein the fluid sample comprises an aqueous solution, the at least one component comprises an organic. Furthermore, in a particular embodiment of the invention, the first carrier fluid is a liquid, and the substantially inert purge fluid comprises a gas. Examples of organics which can be separated from a fluid sample and measured with the apparatus of the invention include non-volatile organic compounds, and volatile organic compounds, such as benzene, toluene, xylene, perchloroethylene, and trichloroethylene, to name only a few.

Naturally, the membrane of the apparatus of the invention can comprise a symmetrical or asymmetrical structure. In a particular embodiment, the at least one membrane is at least one hollow fiber having a bore and an outer surface, and the at least one fiber is contained within a shell, such that the bore of the at least one hollow fiber membrane defines the feed chamber, and the shell and the outer surface of the hollow fiber define the exit chamber. Furthermore, in a particular embodiment of the apparatus of the invention, a plurality of hollow fiber membranes are enclosed in the shell, forming a membrane module.

Moreover, the present invention extends to an apparatus for separating and analyzing at least one component of a fluid sample, as set forth above, wherein the membrane comprises nonporous hydrophobic material. Numerous nonporous hydrophobic materials have applications as the membrane of the apparatus of the invention. Examples of such materials include, but certainly are not limited to polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, or polyethers. In a particular embodiment of the invention in which the at least one membrane is a hollow fiber, the at least one membrane is comprised of polydimethylsiloxane, has an inner diameter (I.D.) of 0.305 mm, and an outer diameter (O.D.) of 0.635 mm.

Also, the at least one membrane of the invention can also be a membrane composite comprising a porous membrane having a first and second surface, and a nonporous hydrophobic membrane permanently disposed on the second surface of the porous membrane, such that the first surface of the porous membrane is in fluid registry with the feed chamber, and the nonporous hydrophobic membrane is in fluid registry with the exit chamber. Naturally, numerous materials can be used to form the porous membrane of the membrane composite. Examples of such materials include polypropylene, polyethylene, polytrimethylpentene, polytetrafluoroethylene, polyvinylidene difluoride, or polysulfone, to name only a few. In a particular embodiment of the invention wherein the membrane comprises a membrane composite as described above, the pores of the porous membrane range in size from about 6 to about 500 Å.

In addition, the present invention extends to an apparatus for separating and analyzing at least one component of a fluid sample, as described above, wherein the trap means comprises a column having a first end in fluid communication with the exit chamber, and a second end in fluid communication with the detector. The column is packed with a packing material to which the at least one component can reversibly adsorb, i.e. adsorb to and then subsequently desorb there from. In general, any polymeric or carbon based adsorbent may be used. Examples of such materials include, but are not limited to, "TENAX", silica gel, or a carbon based sorbent such as charcoal, "CARBOTRAP C" (Supelco, Inc.), or "CARBOSIEVE". In a particular embodiment, wherein the at least one component comprises an organic, the column is packed with "CARBOTRAP C" produced by Supelco, Inc. Furthermore, a sorbent having applications in the invention can be comprised of a combination of presently known sorbents.

Moreover, the column of the trap means can be comprised of a material which does not react with the packing material, the at least one component, and the second carrier fluid. Particular examples of materials which can be used to produce column include stainless steel, "TEFLON", polypropylene, or glass, to name only a few. In a particular embodiment of the invention, the trap means comprises a column made of stainless steel, with a length of 15 cm, an outer diameter of 0.53 mm, and is packed with "CARBOTRAP C" (Supelco, Inc.).

Furthermore, numerous releasing means for releasing the at least one component from the trap means are available to the skilled artisan and have applications in the present invention. In a particular example, the releasing means comprises a means for heating the packing material in the column after the at least one component has reversibly adsorbed to the packing material. As a result of heating, the at least one component desorbs from the packing material, and is flowed to the detector for measurement and analysis via the second carrier fluid. Numerous means for heating the packing material are available to the skilled artisan. In a particular embodiment of the invention, wherein the at least one component is an organic which has reversibly adsorbed to the packing material, the heating means comprises a power supply electrically connected to the column, so that an electric current can be conducted through the column. As a result of this current, the column undergoes resistive heating, which in turn heats the packing material in the column. The organics then desorb from the packing material and are flowed into the detector via the second carrier fluid. Other heating means having applications herein include bombarding the column with electromagnetic radiation, and placing a flame adjacent to the column, such that the column heats up. Furthermore, another desorption means having applications herein is a solvent which is contacted with the trap means, such that the solvent elutes the trapped component from the trap means.

Likewise, numerous detectors have applications in an apparatus of the invention. Examples of applicable detectors include a gas chromatograph, a high performance liquid chromatograph, a gas chromatograph coupled to a mass spectrometer, a capillary electrophoresis instrument, a mass spectrometer, a total organic carbon analyzer (TOC) or an IR, UV, Raman or fluorescence spectrometers, to name only a few.

The present invention further extends to a process for separating and analyzing at least one component of a fluid sample. In a particular embodiment, the process of the invention is practiced with an apparatus comprising a feed chamber having an entrance and an exit, a first flow means for flowing a first carrier fluid through the feed chamber, means for injecting a pulse of fluid sample into the flow first carrier fluid such that the pulse of fluid sample enters the feed chamber, an exit chamber downstream from the feed chamber, at least one membrane through which the at least one component can selectively permeate there through, wherein the at least one membrane is located between the feed chamber and the exit chamber, and is fluid registry with the feed chamber and the exit second chamber, means for flowing a substantially inert purge fluid into the feed chamber after the pulse of fluid sample has passed through the feed chamber, a trap means located downstream from the exit chamber and in fluid communication therewith, wherein the at least one component that permeates through the at least one membrane can be trapped, a releasing means connected to the trap means, wherein the releasing means can release the at least one component trapped in the trap means, a detector in fluid communication with the trap means, wherein the detector detects the at least component released from the trap means, and a second flow means for flowing the at least one component which permeates through the at least one membrane and enters the exit chamber, from the exit chamber to the trap means, and then upon release from the trap means, to the detector. The process of the invention comprises the steps of:

a) flowing the first carrier fluid through the feed chamber;

b) injecting the pulse of fluid sample into the first carrier so that the fluid sample enters the feed chamber;

c) flowing a substantially inert purge fluid into the feed chamber after the fluid sample has passed through the feed chamber;

d) trapping the at least one component which permeates through the membrane to the exit chamber;

e) releasing the trapped at least one component; and f) detecting the at least one component.

Hence, with the process of the invention, a pulse of fluid sample having a discreet volume ranging from about 1 µl to and including 10 ml can be analyzed.

Naturally, in the process of the invention, the at least one membrane can be symmetrical or asymmetrical in structure. In a particular embodiment, the at least one membrane of the process comprises at least one hollow fiber having a bore and an outer surface, and the at least one fiber is contained within a shell, such that the bore defines the feed chamber, and the shell and the outer surface of the at least one hollow fiber define the exit chamber. Furthermore, also encompassed by the present invention is a fiber module comprising a plurality of hollow fiber membranes surrounded by the shell. In a particular embodiment of the invention, the at least one hollow fiber membrane comprises an inner diameter of 0.305 mm, and an outer diameter of 0.635 mm.

Furthermore, in an embodiment of the invention, a membrane module is used which comprises a plurality of membranes housed within the shell. Hence, the surface area of the at least one membrane can be increased, which increases the efficiency of the present invention.

Furthermore, as explained above, the membrane is comprised of a material through which the at least one component can selectively permeate. In a particular embodiment, wherein the fluid sample comprises an aqueous solution, and the at least one component comprises an organic, the membrane of the invention comprises a nonporous hydrophobic material. Examples of nonporous hydrophobic materials having applications as membranes herein include polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, or polyethers, to name only a few. In a preferred embodiment, the at least one membrane of the process of the invention comprises polydimethylsiloxane (silicone rubber).

Moreover, the membrane of the process of the invention can also be a membrane composite, which comprises a porous membrane having a first and second surface, and a nonporous hydrophobic membrane permanently disposed on the second surface of the porous membrane, such that the first surface of the porous membrane is in fluid registry with the feed chamber, and the nonporous hydrophobic membrane is in fluid registry with the exit chamber. Numerous materials can be used in a porous membrane of a membrane composite having applications herein. Examples of such materials include, but are not limited to, polypropylene, polyethylene, polytrimethylpentene, polytetrafluoroethylene, polyvinylidene difluoride, or polysulfone. Furthermore, the size of the pores of the porous membrane can vary, depending upon the types and sizes of organics to be removed from a fluid sample and analyzed. In particular, the size of the pores can range from about 6 to about 500 Å. Naturally, the nonporous hydrophobic membrane of the membrane composite can comprise polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, or polyethers. In a particular embodiment, a membrane composite of the invention comprises a polypropylene membrane having first and second surfaces and a layer of polydimethylsiloxane permanently disposed on the second surface of the polypropylene membrane.

Also, numerous means for creating a flow of the first carrier fluid through the feed chamber are available to the skilled artisan and have applications herein. For example, one such means comprises providing a first reservoir for holding the first carrier fluid, wherein the first reservoir is in fluid communication with the feed chamber, and a pump which is in fluid communication with the first reservoir. The pump, such as a peristaltic pump, a gear pump, or a mechanical pump, can be used to pump the first carrier fluid from the first reservoir and ultimately through the feed chamber. Another method would be to place the first carrier fluid under pressure in the first reservoir, and a valve upstream from the feed chamber and downstream from the first reservoir. When the valve is opened, the pressure of the first carrier fluid in the first reservoir would cause the first carrier fluid to flow from the first reservoir and ultimately through the feed chamber. Still another means involves providing a vacuum means downstream of the exit of the feed chamber and in fluid communication therewith. The vacuum means would draw the first carrier fluid from the first reservoir and through the feed chamber, thus creating a flow of the first carrier fluid.

In addition, the step of the process of the invention which involve injecting the pulse of fluid sample into feed chamber, can be accomplished by numerous means are readily available and understood by the skilled artisan. In a particular example, the step involves providing a multi-port valve located downstream the first reservoir and upstream from the feed chamber, and in fluid communication therewith. The multi-port valve comprises a first port for injecting the pulse of fluid sample into the flow of the first carrier fluid. As a result, the pulse of fluid sample is injected into the flow of the first carrier fluid and carried into the feed chamber. Examples of a first carrier fluid of the invention include, but are not limited to water, water with salt or other additives, an organic solvent, a gas such as nitrogen, carbon dioxide, argon, or neon, or a mixture of gas and liquid.

Moreover, in a particular embodiment of the invention, the step of flowing the substantially inert purge fluid into the feed chamber after the pulse of fluid sample enters the feed chamber comprises providing a switching valve which is upstream of the first reservoir and downstream from the multi-port valve, and is in fluid communication with the multi-port valve and the first reservoir. This step also comprises providing a second reservoir for holding the purge fluid, wherein the second reservoir is in fluid communication with the switching valve, and a means for operating the switching valve such that the first carrier fluid is prevented from entering the feed chamber after the after the pulse of fluid sample has passed through the feed chamber, and the substantially inert purge gas is permitted to flow from the second reservoir into the feed chamber. In the feed chamber, the purge gas disrupts the boundary layer which develops on the membrane, and purges any organics remaining in the membrane. Numerous means for operating the switching valve, such as a microprocessor in communication with the switching valve, or operating the valve manually, are readily available to the skilled artisan. Furthermore, examples of substantially inert purge fluids which have applications herein include nitrogen, carbon dioxide, helium, or neon, to name only a few.

In addition, the present invention extends to a process for separating and analyzing at least one component of a fluid sample as described above, wherein the second flow means comprises a third reservoir which holds the second carrier fluid, wherein the third reservoir is in fluid communication with the exit chamber. In a particular embodiment, the second carrier fluid is held under pressure in the third reservoir, and a valve is located downstream from the third reservoir and upstream from the exit chamber, such that the valve is in fluid communication with the third reservoir and the exit chamber. When the valve is opened, the pressure of the second carrier fluid causes the second carrier fluid to flow from the third reservoir, through the exit chamber, through the trap means, and ultimately to the detector. Thus, any component which passes through the membrane and enters the exit chamber will be carried to the trap means, and ultimately to the detector. Another means for creating a flow of the second carrier fluid as described above include a pump, such as a peristaltic pump, downstream from the third reservoir and upstream of the exit chamber, so that the second carrier fluid is pumped from the third reservoir, and a flow of the second carrier fluid through the exit chamber, trap means, and to the detector is created. Still another means for creating the flow of the second carrier fluid involves providing a vacuum pump downstream of the detector, such that the vacuum draws the second carrier fluid from the third reservoir, through the exit chamber, the trap means, and to the detector. Examples of the second carrier fluid having applications herein include, nitrogen, hydrogen or helium, to name only a few. In some instances, organic solvents such as hexane, methanol or acetonitrile may also be used.

Furthermore, the present invention extends to a process for separating and analyzing at least one component in a fluid sample as described above, wherein the trap means comprises a column having a first end in fluid communication with the exit chamber, and a second end in fluid communication with the detector. The column of the trap means is packed with a packing material to which the at least one component can reversibly adsorb. In a particular embodiment, wherein the fluid sample comprises an aqueous solution and the at least one component is an organic, the column is made of a material that does not react with the packing material or the organic, e.g., stainless steel, Teflon, polypropylene, or glass to name only a few. Furthermore, numerous packing materials can be used to reversibly adsorb organics. Examples of such materials include, but certainly are not limited to "TENAX", silica gel, or a carbon based sorbent such as charcoal, "CARBOTRAP C" (Supelco, Inc. Supelco, Pa.), "CARBOSIEVE" , or "CARBOPACK". Further, the packing material of the column can be comprised of a combination of these sorbent materials. Still other sorbents can be bonded phases such as C18, C8, etc., which need to be desorbed by an organic solvent. In a particular embodiment of the invention, the column is comprised of stainless steel, has a length of 15 cm and an outer diameter of 0.53 mm, and packing material comprises "CARBOTRAP C".

In addition, the present invention extends to a process for separating and analyzing at least one component of a fluid sample, as described above, wherein the step of releasing the at least one component from the trap means comprises providing means for heating the packing material such that the at least one component, e.g., an organic, can desorb from the packing material, and then be flowed to the detector for analysis via the flow of the second carrier fluid. Numerous means of releasing trapped component from the trap means are available and readily apparent to the skilled artisan. In a particular example, where the at least one component is an organic, the packing material can be heated. As a result of such heating, a component of the fluid sample, such as an organic can readily desorb from the packing material. A wide variety of means for heating the packing material are available to one of ordinary skill in the art and have applications herein. Particular means of heating the packing material include a power supply electrically connected to the column. If the column conducts an electric current, a current conducted through the column will cause the column to heat, which in turn heats the packing material. Other means of heating the packing material include bombarding the column with electromagnetic radiation, or placing a flame adjacent to the column. Alternatively, a solvent can be used to desorb the component from the packing material. In such an embodiment, the solvent is permitted to contact the packing material, such as flowing the solvent through the column. Examples of such solvents include, but are not limited to methanol, ethanol, hexane, toluene, aliphatic hydrocarbons, alcohols, aromatic solvents, methylene chloride, aqueous buffers, or other solvents used in normal and reverse phase elution. The solvent desorption is particularly applicable in the separation and analysis of non-volatile compounds that can not be removed by heating.

Furthermore, numerous detectors have applications in the process of the invention, including a gas chromatograph, a high performance liquid chromatograph, a gas chromatograph coupled to a mass spectrometer, a capillary electrophoresis instrument, a mass spectrometer, a total organic carbon analyzer, or an infra red (IR), ultraviolet (UV), Raman or fluorescence spectrometer, to name only a few.

Accordingly, a principal object of the invention is to provide an apparatus and process for separating and analyzing at least one component of a fluid sample, wherein the pulse of fluid sample comprises a discreet volume, and it is not necessary to flow the fluid sample through the feed chamber continuously.

Another object of the invention is to provide an apparatus and process for separating and analyzing at least one component of a fluid sample, and using a membrane extraction, which is not dependent upon forming an equilibrium across the membrane. As a result, response time for obtaining accurate measurements of the quantity of component in the fluid sample is decreased relative to the response time needed to obtain accurate measurements in a membrane extraction instrument which is dependent upon an equilibrium across the membrane.

Yet another object of the present invention is to disrupt the boundary layer that develops upon the membrane in the feed chamber. As a result of this disruption, the component in the fluid sample is spared the heretofore necessity of diffusing across the boundary layer, and can diffuse directly into and through the membrane. Hence, the lag time between injecting the pulse of fluid sample into the apparatus and detection of the at least one component in the fluid sample is dramatically decreased relative to heretofore known membrane extraction techniques.

Yet still another object of the invention is enable the analysis of fluid samples having a discreet volume These and other aspects of the present invention will be better appreciated by reference to the following drawings and Detailed Description.

DETAILED DESCRIPTION OF THE INVENTION

Figure 1:
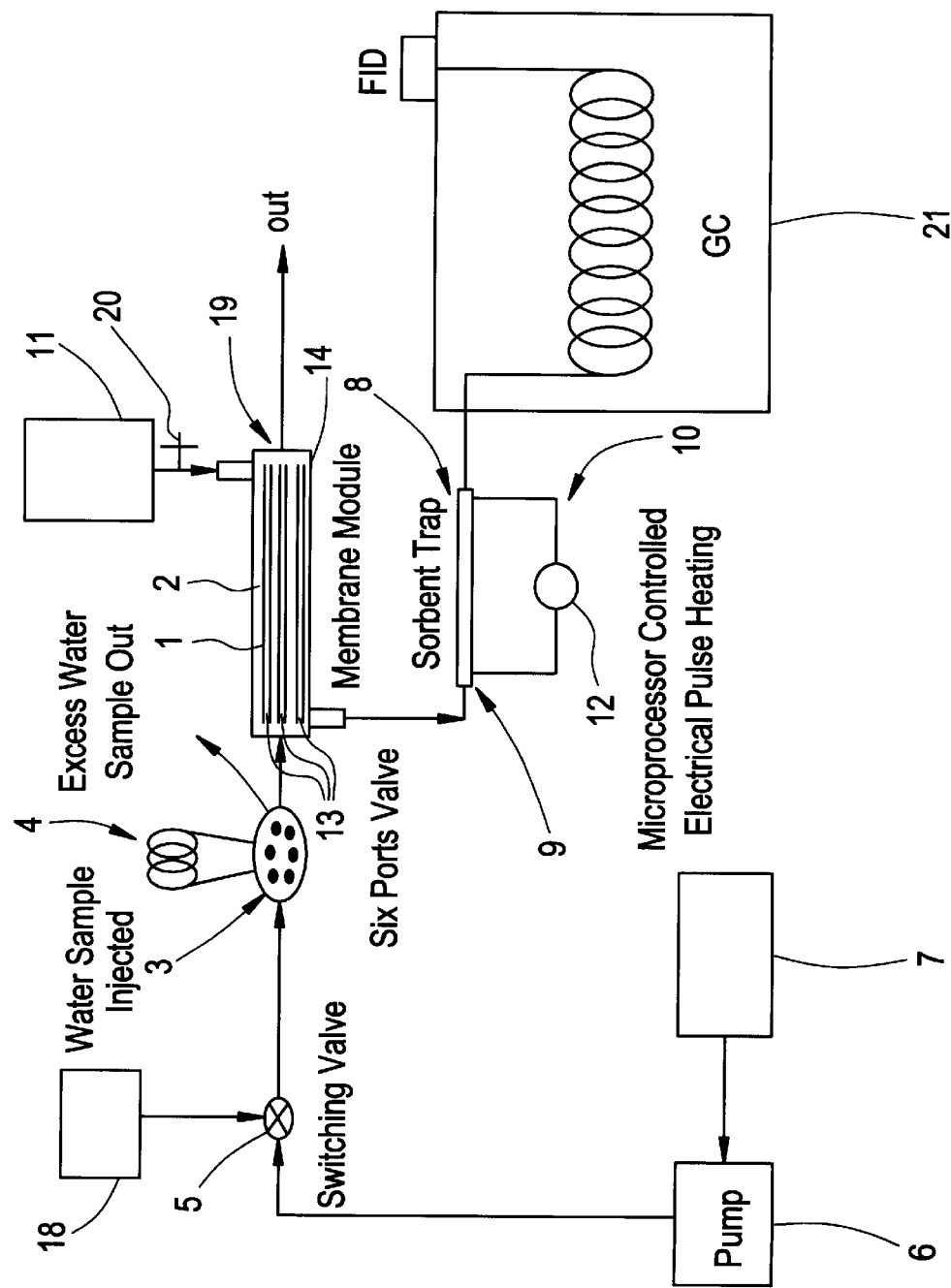
FIG. 1 is a schematical view of an apparatus of the Invention.

As described above, the present invention broadly extends to an apparatus for separating and analyzing at least one component of a fluid sample, the apparatus comprising:

a feed chamber having an entrance and an exit, a first flow means for flowing a first carrier fluid through the feed chamber;

means for injecting a pulse of fluid sample into the flow first carrier fluid such that the pulse of fluid sample enters the feed chamber;

a exit chamber downstream from the feed chamber;

at least one membrane through which the at least one component can selectively permeate there through, wherein the at least one membrane is located between the feed chamber and the exit chamber, and is fluid registry with the feed chamber and the exit second chamber;

a detector in fluid communication with the trap means, wherein the detector detects the at least component released from the trap means; and a second flow means for flowing the at least one component which permeates the at least one membrane and enters the exit chamber to the detector.

Moreover, the present invention extends to a process for separating and analyzing at least one component of a fluid sample, practiced with an apparatus comprising:

a feed chamber having an entrance and an exit, a first flow means for flowing a first carrier fluid through the feed chamber;

means for injecting a pulse of fluid sample into the flow first carrier fluid such that the pulse of fluid sample enters the feed chamber;

a exit chamber downstream from the feed chamber;

at least one membrane through which the at least one component can selectively permeate there through, wherein the at least one membrane is located between the feed chamber and the exit chamber, and is fluid registry with the feed chamber and the exit second chamber;

a detector in fluid communication with the trap means, wherein the detector detects the at least component released from the trap means; and a second flow means for flowing the at least one component which permeates the at least one membrane and enters the exit chamber to the detector, the process comprising the steps of:

a) flowing the first carrier fluid through the feed chamber;

b) injecting the pulse of fluid sample into the first carrier so that the pulse of fluid sample enters the feed chamber;

f) detecting the at least one component which passes through the at least one membrane.

Also, in describing the apparatus and process of the invention, numerous terms and phrases are used throughout the specification and claims. Definitions of these terms and phrases are provided below:

As used herein, the term "permanently disposed" as applied to the deposition of the nonporous hydrophobic membrane to the porous membrane means that the nonporous membrane is sufficiently bonded to the porous membrane such that the nonporous hydrophobic membrane can not be removed from the porous membrane.

The term "organic" or in the plural "organics" refers to volatile and non-volatile organic compounds. The phrase "volatile organic compound" refers to an organic compound whose vapor pressure is greater than standard atmospheric pressure. Specific examples of volatile organic compounds include toluene, xylene, acetone, trichloroethylene, trichloroethane, methanol, ethanol, methyl ethyl ketone, carbon tetrachloride, vinyl chloride, isobutanol, chlorobenzene, butane, pentane, hexane, octane, fluorinated hydrocarbons (CFC-11, CFC-12, CFC-113, CFC-114, CFC-115, etc.), HCFC ($C_2HCl_2F_3$), perchloroethylene, to mention but a few. Those skilled in the art will recognize the above list of examples is not exhaustive.

The term "porous membrane" refers to a hydrophobic or a hydrophilic, or hydrophobic on one side and hydrophilic on the other side material containing pores having a diameter between about 6 and about 500 Å. Preferably, the membrane is provided in the form of a hollow fiber.

The term "hydrophobic" describes a substance which neither absorbs nor adsorbs water. Preferred hydrophobic membranes include porous polyethylene, porous polypropylene, porous polyamides, porous polyimides, porous polyetherketones, porous polyvinylidene fluoride, porous polyvinyl chloride, porous polysulfone, porous polyethersulfone, and porous polytetrafluoroethylene (PTFE). In a specific embodiment, the hydrophobic membrane is a porous propylene membrane, "CELGARD" (Hoechst Celanese, SPD, Charlotte, N.C.). These membranes may be isotropic (like "CELGARD"), or they may be asymmetric, as in ultrafiltration membranes. In an embodiment of the invention, the hydrophobic membranes may be "CELGARD" X-10 and "CELGARD" X-20. Those skilled in the art will recognize that the above list of examples is not exhaustive.

The phrase "selectively permeate" as used herein to describe a membrane refers to the membranes ability to permit the at least one component of a fluid sample, but not the fluid sample itself or the first carrier fluid, to pass through the membrane.

As used herein, the phrase "substantially inert" in describing a fluid such as a gas or liquid refers to the chemical unreactivity of the fluid with chemical species that make contact with the fluid.

As used herein, the term "pulse" referring to a volume of fluid sample injected into the stream of a carrier fluid. Generally, the volume ranges from about 1 μ to about 10 ml, depending upon the application.

As used herein, the phrases "lag time" and "response time" refer to the length of time over which the system continues to respond after a sample pulse has been introduced into the feed chamber.

As used herein, the phrase "boundary layer" refers to a layer of fluid sample which develops on the surface of membrane in the feed chamber. If the boundary layer is not removed, any components of the fluid sample which are to pass through the membrane must first pass through the boundary layer, increasing the response time.

A chemical specie, such an organic, which can "reversibly adsorb" to a material refers to the binding or attraction of the chemical specie to the material in a manner such that when a sufficient amount of energy is applied to the chemical specie adsorbed to the material, the attraction of the chemical specie for the material markedly decreases, and the chemical specie becomes free of the material.

The phrase "aqueous solution" as used herein refers to a mixture that contains water with other components and contaminants. Examples of aqueous solutions include groundwater, effluent, rainwater, or tap water, to name only a few.

The phrase "in fluid communication" as used herein refers to the ability of a fluid to flow from one component to another component.

The phrase "electrically connected" as used herein refers to a connection between two components through which an electrical current can pass.

As explained above, FIG. 1 is a schematical view of the apparatus of the invention. In particular, the membrane in this embodiment of the invention is hollow fiber membrane (1), and is comprised of a nonporous hydrophobic material. Examples of nonporous hydrophobic materials having applications in the invention include include polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, or polyethers, to name only a few. In a preferred embodiment, the at least one hollow fiber membrane (1) of the process of the invention comprises polydimethylsiloxane (silicone rubber), has an inner diameter (I.D.) of 0.305 mm and an outer diameter (O.D.) of 0.635 mm. Furthermore, a membrane module comprising a plurality of such membranes has applications herein, and is schematically s shown in FIG. 1.

Furthermore, referring again to FIG. 1, shell (14) surrounds the at least one hollow fiber membrane (1). As a result, exit chamber (2) is formed by the outer surface of hollow fiber membrane (1) and shell (14). In a preferred embodiment of the invention, a membrane module (19) which comprises a plurality of hollow fiber membranes (1) is used. Membrane module (19) increases the surface area of membrane in fluid registry with feed chamber (13).

Figure 2:
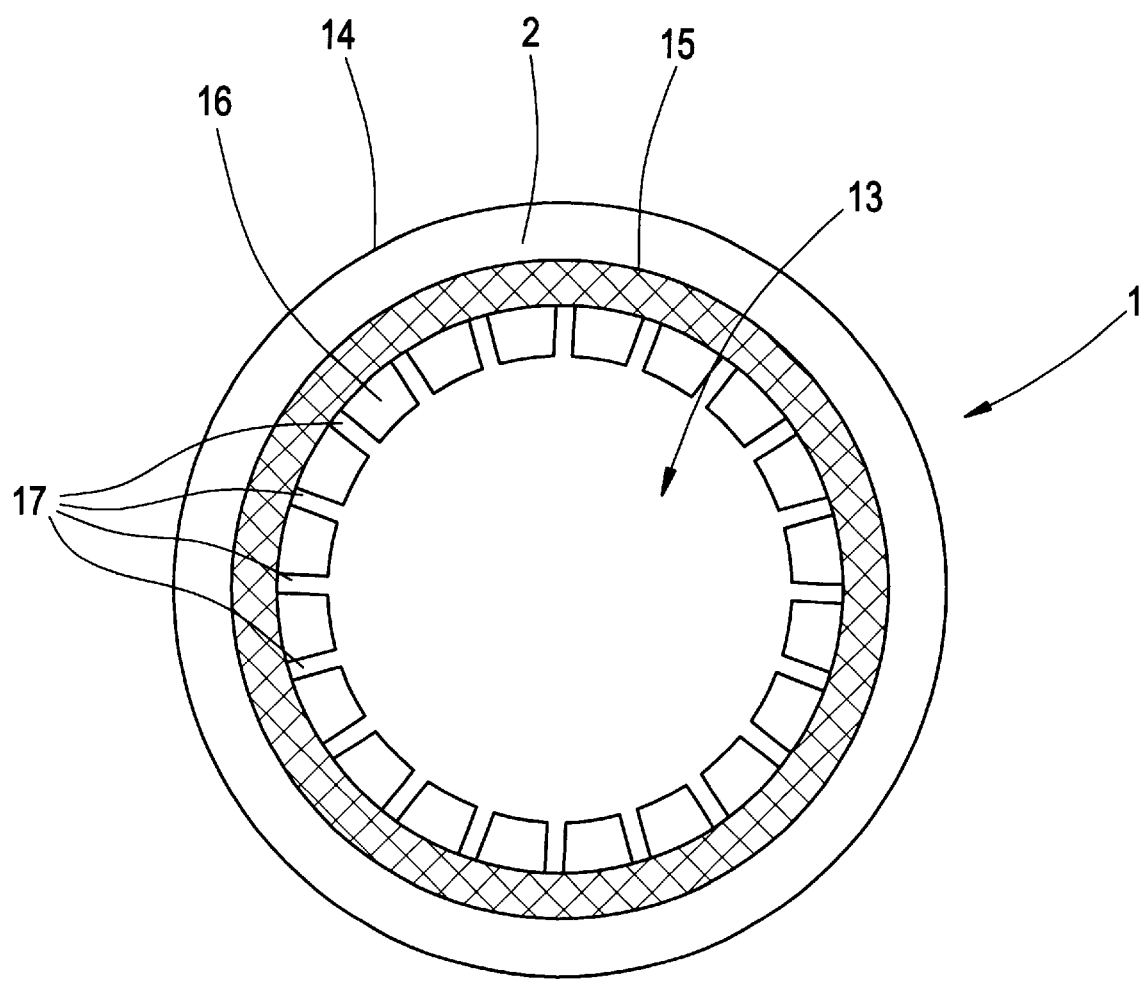
FIG. 2 is a cross sectional schematical view of a hollow fiber membrane composite having applications in the present Invention.

FIG. 2 is a schematical cross sectional view of another embodiment of hollow fiber membrane (1) having applications in the invention. In particular, hollow fiber membrane (1) schematically and cross sectionally set forth in FIG. 2 is a membrane composite comprising porous hydrophobic membrane (16) and nonporous hydrophobic membrane (15) permanently disposed on the outer surface of porous membrane (16), i.e., opposite of the bore of the hollow fiber membrane. Numerous materials have applications as porous membrane (16) of the invention. Particular examples of such materials include porous polyethylene, porous polypropylene, porous polyamides, porous polyimides, porous polyetherketones, porous polyvinylidene fluoride, porous polyvinyl chloride, porous polysulfone, porous polyethersulfone, and porous polytetrafluoroethylene (PTFE). Furthermore, the bore of hollow fiber membrane (1) forms feed chamber (13). Consequently, porous hydrophobic membrane (16) is in fluid registry with feed chamber (13) while the nonporous hydrophobic membrane (15) is in fluid registry with exit chamber (2). Furthermore, shell (14) and nonporous hydrophobic membrane (15) of fiber (1) form exit chamber (2). Pores (17) of porous membrane (16) can have a diameter between about 6 and about 500 Å, depending upon the application.

In another embodiment of the invention, the at least one hollow fiber comprises a plurality of hollow fiber membranes (1) of a fiber membrane module (19) of FIG. 1 such that the pulse of fluid sample enters the bores of all the hollow fibers of membrane module (19) concurrently.

Referring again to FIG. 1, multi-port valve (3) is in fluid communication with feed chamber (13) of hollow fiber membrane (1). Optionally, multi-port valve (3) comprises sample loop (4), which permits one of ordinary skill to inject pulses of fluid samples having varying volumes into a flow of first carrier fluid upstream of feed chamber (13). Hence, fluid samples ranging in volume from 1 μ to and including 10 ml can be readily analyzed with the present invention. Furthermore, first reservoir (7) holding the first carrier fluid is in fluid communication with pump (6), which is in turn, in fluid communication with multi-port valve (3). Various types of pumps, including a peristaltic pump, a mechanical pump and a gear pump, to name only a few, have applications herein. Hence, when pump (6) pumps first carrier fluid from first reservoir, (7), through multi-port valve (3) and through the bore of hollow fiber membrane (1), a continuous flow of first carrier fluid through feed chamber (13) is formed. In addition, the apparatus of invention can comprise switching valve (5) which is downstream from first reservoir (7) , upstream from multi-port valve (3) and in fluid communication with first reservoir (7) and multi-port valve (3). Switching valve (5) is also in fluid communication with second reservoir (18), which holds the substantially inert purge fluid. When switching valve (5) is operated, the first carrier fluid is prevented from entering feed chamber (13) after the fluid sample has passed through, and the substantially inert purge fluid is permitted to enter feed chamber (13). Examples of first carrier fluids having applications include water, water with salt or other additives, organic solvents, nitrogen, carbon dioxide, argon, neon, or a combination thereof. Furthermore, the substantially inert purge fluid can be comprised of nitrogen, carbon dioxide, helium, or neon. In a preferred embodiment of the invention, wherein the fluid sample comprises an aqueous solution and the at least one component comprises an organic, the first carrier fluid comprises distilled water and substantially inert purge fluid comprises nitrogen. However, as explained above, numerous other means of creating a flow of the first carrier fluid through the feed chamber have applications herein.

Further referring to FIG. 1, third reservoir (11) for holding the second carrier fluid is in fluid communication with exit chamber (2) of the invention. Moreover, exit chamber (2) is in fluid communication with trap means (9). As explained above, when the fluid sample comprises an aqueous solution, and the at least one component comprises an organic, trap means (9) comprises column (8) packed with a packing material to which the organic reversibly adsorbs.

Numerous materials can be used to form column (8) of the invention, including, but not limited to, stainless steel, glass, or "TEFLON". Furthermore, numerous packing materials, such as "TENAX", silica gel, or a carbon based sorbent such as charcoal or "CARBOTRAP C" (Supelco, Inc.), "CARBOSIEVE" or "CARBOPACK" to name only a few, have applications herein. In a particular embodiment, column (8) is comprised of stainless steel, has a length of about 15 cm, an outer diameter of about 0.53 mm, and is packed with "CARBOTRAP C".

Moreover, as explained above, after the pulse of fluid sample fluid has passed through feed chamber (13), an inert purge fluid enters feed chamber (13). There, the substantially inert purge fluid disrupts the boundary layer on the surface of the membrane in fluid registry with feed chamber (13), and purges any organics remaining in the membrane, thus reducing lag time. Hence, discreet volumes of fluid samples can be quickly and accurately analyzed with the invention without the necessity of setting up a steady state of component traversing the membrane. In this particular embodiment of the invention, second reservoir (18), which is fluid communication with switching valve (5) contains the substantially inert purge fluid under pressure. When switching valve (5) is switched, the substantially inert purge fluid escapes from second reservoir (18) enters multi-port valve (3) and enters feed chamber (13). Examples of substantially inert purge fluid having applications herein include, but are not limited to, nitrogen, carbon dioxide, helium, or neon. In a particular example of the invention, wherein the fluid sample comprises water, the at least one component comprises an organic, and the first carrier fluid comprises distilled water, the substantially inert purge fluid comprises nitrogen.

Still referring to FIG. 1, exit chamber (2) is in fluid communication with the first end of trap means (9). As explained above, numerous trap means having applications in the invention. In an embodiment of the invention wherein the component comprises an organic, trap means (9) comprises column (8) which is packed with a material to which an organic reversibly adsorbs. Column (8) can be made of any material which does not chemically react with the packing material and the organic. Examples of materials which can be used as column (8) herein include glass, stainless steel, polypropylene or Teflon, to name only a few. Furthermore, numerous packing materials can be used in column (8), including but not limited to "TANEX" silica gel, or a carbon based sorbent such as charcoal, "CARBOTRAP C" (Supelco, Inc.), "CARBOSIEVE", "CARBOPACK", etc. In a particular embodiment of the invention, column (8) is comprised of stainless steel, has a length of 15 cm, an outer diameter of 0.53 mm, and is packed with "CARBOTRAP C". For solvent desoprtion, suitable material such as bonded phases, $C_8$, $C_{18}$ can be used. Solvent desorption is also applicable in the separation and analysis of large non-volatile molecules, such as polycyclic aromatic hydrocarbons, pesticides, PCBs, etc. from a fluid sample.

In addition, the second end of trap means (9) is in fluid communication with detector (21). In the embodiment of the invention schematically shown in FIG. 1, detector (21) comprises a gas chromatograph. However, any detector presently known, or subsequently discovered, has applications herein. Particular examples include a gas chromatograph, a high performance liquid chromatograph, a gas chromatograph coupled to a mass spectrometer, a capillary electrophoresis instrument, a mass spectrometer, a total organic carbon analyzer, or an infra red (IR), ultraviolet (UV), Raman or fluorescence spectrometer, to name only a few.

Furthermore, as explained above, and still referring to FIG. 1, the present invention also comprises a second flow means for flowing the at least one component which permeates the membrane and enters exit chamber (2), from the exit chamber (2) to trap means (9), and then ultimately from trap means (9) to detector (21). In the embodiment of the invention schematically shown in FIG. 1, the second flow means comprises third reservoir (11) holding the second carrier fluid under pressure, wherein third reservoir (11) is in fluid communication with exit chamber (2). When valve (20) is opened, the pressure causes the second carrier fluid to flow from third reservoir (11) into exit chamber (2), then from exit chamber (2) through trap mans (9), and then ultimately to detector (21). As a result, any component of the fluid sample which traverses through the membrane and enters exit chamber (2) is flowed via the second carrier fluid to trap means (9), where the component is trapped. When the component is released from trap means (9), the second carrier fluid flows the component into detector (21), where the component is analyzed. In a particular example, wherein the at least one component comprises an organic, the second carrier fluid comprises nitrogen, carbon dioxide, neon or argon.

Moreover, as explained above, the present invention comprises releasing means (10) to release the component trapped in the trap means for analysis in the detector. In a particular embodiment of the invention, wherein the component comprises an organic, the organic is reversibly adsorbed to a packing material in column (8) of trap means (9). When energy is added to the packing material, the organic desorbs from the packing material, and flows into detector (21) for analysis via the second carrier fluid. In a particular embodiment of the invention, releasing means (10) comprises power supply (12) electrically connected to column (8), wherein column (8) is comprised of stainless steel. When a current is passed through column (8), column (8) undergoes resistive heating, which in turn heats the packing material, and permits the at least one component to desorb from the packing material. Other means of heating column (8) of trap means (9) are readily available to the skilled artisan and include bombarding the column with electromagnetic radiation, e.g., microwaves, or placing a flame adjacent to the column.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Pulse Introduction Membrane Extraction for Measurement of Organics in Water

Introduction

Measurement of organics in water usually involves a separation step where the organics are first extracted from the matrix. Direct injection of aqueous fluid samples have been attempted, but this method is applicable only to the analysis of high concentration fluid samples as the injection volume is limited to a few microliters. Popular analytical techniques used for organics analysis are purge and trap, head space analysis, solid phase extraction and solid phase micro-extraction. All these methods first isolate the organics from water prior to analysis by GC or GC/MS.

Purge and trap has emerged as the leading technique for organics measurement because of its low detection limits and high precision. It is a dynamic head space procedure carried out by purging the organics from water with the help of an inert gas such as $N_2$. The purged organics are trapped and concentrated in a sorbent trap. Subsequently, these compounds are injected into a GC or a GC/MS for analysis. The purge chamber is sometimes heated to an elevated temperature to increase the vapor pressure of compounds of lower volatility. Purge gas is introduced into the bottom of the purge chamber and dispersed into fine bubbles to ensure good gas-water contact. The trap is usually a cooled sorbent trap packed with Tenax, silica gel and charcoal. The desorbed analytes are refocused either on a cryogenic trap or on the GC column itself to generate a narrow injection band. The trapping stage (or stages) usually require cryogenic cooling.

Although purge and trap is an excellent technique, it is a fairly involved process that includes several distinctive steps. This makes the instrumentation fairly cumbersome with complicated plumbing for purging, trapping cryogenic cooling, etc. Cold spots in the plumbing also result in carryover problems and memory effects. Often blanks have to be run between analysis of the fluid samples.

In recent years, membranes have been used in a variety of separation processes such as dialysis, ultra-filtration, osmosis and dehumidification[1]. Membranes have been used to separate organics from both air and water in pollution-control devices. In case of air analysis, the organics migrate from a gaseous phase to another gaseous phase through a membrane. This phenomenon is called gas permeation. In case of water analysis, the analytes from water are selectively transported to a gaseous phase across the membrane and vaporized in this phase. This technique is called pervaporation. Pervaporation has been used in industry as a separation technique for the recovery of liquid mixtures. Numerous experimental and theoretical investigations have been published on this subject[2,3].

Membranes have been used in analytical instrumentation as well. Membrane interface for fluid sample introduction into mass spectrometry has received most attention[4-6]. Membrane separations coupled with other detection devices have also been studied[7]. The analytes can selectively permeate through the membrane while the bulk matrix of water/air as well as other interferences are eliminated. In this method, a fluid such as water or air continuously flows through a membrane module containing multiple hollow fiber membranes. The permeated organics that pass through the membrane are entrained by a second carrier fluid, such as an inert gas, concentrated in a micro sorbent trap, and injected onto a GC column. However, this method is limited in that it requires a fluid sample to flow constantly through the membrane module. As a result, it is unsuited for analyzing an individual fluid sample as done in purge and trap. A different instrument configuration that allows introduction of discreet volumes of sample is necessary.

Disclosed herein is a novel Pulse Introduction Membrane Extraction (PIME) apparatus and method for separating and analyzing at least one component in a fluid. In this technique, the organics are separated from the aqueous phase via membrane permeation and the substantially inert purge fluid disrupts a boundary layer on the surface of the membrane in the feed chamber, and purges the membrane of any organics that remain in the membrane. This reduces sample carry-over and lag time so that the next analysis can be carried out quickly. Further, the pulse permits the evaluation of fluid samples having a discreet volume. Organics which permeate through the membrane are pneumatically transported to a sorbent trap. Although any type of sorbent or cryogenic trapping system may be used, a micro-sorbent trap referred to as the microtrap is used here. This allows the combination of the trapping and injection steps into one step. The trapped organics are then injected into a detector, such as a GC by rapid desorption of the microtrap.

Mechanism of Membrane Permeation

The isolation of organics from water using polymeric membrane medium involves five steps[1]:

1. Analytes from bulk water sample diffuse to the membrane interface;
2. The organics dissolve into the membrane;
3. Dissolved organics diffuse through membrane under a concentration gradient;
4. The analytes desorb into the vapor phase at the interface of membrane and downstream gas;
5. The vapor permeates through the interface into the stripping gas.

Fick's law of diffusion has been widely used to describe membrane permeation under steady state conditions. It attempts to predict the permeation flux as a function of experimental conditions. For one-dimensional transport in a direction normal to the membrane interface:

$$J=D(\partial C/\partial X)$$

where J is the rate of diffusion of the permeant gas through a unit reference area, D is the diffusion coefficient for a specific permeant-membrane system at a certain temperature, and C is the concentration of the permeant in the membrane at a position coordinate X. The concentration gradient can be obtained from Fick's second law:

$$\partial C/\partial t=\partial(D\partial C/\partial X)/\partial X$$

where $\partial C/\partial t$ is the rate of change in concentration with time, t, at a position coordinate X. The driving force in pervaporation is the concentration gradient between liquid and surrounding gas.

To optimize the membrane extraction process, several factors should be taken into consideration. These include chemical and physical properties of the membrane material, configuration of membrane module and fluid sample feeding conditions such as flow rate and injection volume. Since the permeability of organics directly effects the instrument sensitivity, these parameters are important. Hence, continuous flow of the fluid sample to produce a steady state is not effective in separating and analyzing a sample fluid having a discreet volume. The methods set forth below enable one of ordinary skill in the art to use membrane permeation without a continuous flow of fluid sample through the feed chamber.

Methods

The schematic diagram of an apparatus of the invention is shown in FIG. 1. Since hollow fibers provide large surface to volume ratio and high packing densities, hollow fiber membranes were selected to make the membrane module. The membrane used in this research was a non-porous, hydrophobic hollow silicone (poly(dimethylsiloxane)) fiber of 0.305 mm I.D.–0.635 mm. O.D. (Dow Corning Corporation, Midland, Mich., USA) as well as silicone composite with a porous polypropylene support. The membrane module was fitted with multiple membrane fibers. A carrier stream continuously flowed through the membrane module. A multi-port valve was used to inject a water sample onto the carrier fluid which transported the pulse of fluid sample to the membrane module. In this study, water was used as the first carrier fluid. Nitrogen gas was used as the purge fluid which entered the feed chamber after the pulse of fluid sample has passed through the feed chamber. A pump was used to pump the first carrier fluid through the membrane module. The pressure drop inside the membrane module was not significant and a high pressure pump was not necessary.

The pulse of fluid sample was injected using a conventional six port sampling valve (Valco Inc., Houston, Tex.). There is much flexibility as to the size of the pulse of fluid sample to be injected. For lower detection limits a larger volume (5 to 10 ml of water) was used, whereas for high concentration fluid samples, a pulse of fluid sample of 1 $\mu$l was adequate. After the pulse of fluid sample entered the feed chamber and the organics in the pulse of fluid sample entered the membrane, the flow of the first carrier fluid into the feed chamber was replaced with the flow of the $N_2$ purge gas, which disrupted the boundary layer of fluid described above, purged any organics remaining in the membrane. Thus, it completed the permeation process faster, reduced lag time of the measurement process, and analysis could be carried out faster. When the organics pass through the membrane and enter the exit chamber, a flow of $N_2$ carrier fluid (5 to 10 ml/min) in the exit chamber pneumatically transports the extracted organics to the concentration stage.

A micro-sorbent trap referred to as the microtrap was used to concentrate the organics that pass through the membrane. It was heated with a pulse of electric current to desorb the organics as a "concentration pulse" which served as an injection for gas chromatography. The microtrap was made by packing a 15 cm long–0.53 mm O.D. small stainless tubing with "CARBOTRAP C" (Supelco Inc.). Detailed microtrap operations have been published before and are not repeated here in details[15]. The microtrap served as a pre-concentrator as well as an injector and was connected directly to the GC column. The injection was made by heating the microtrap with a pulse of electric current. A current of seven to ten amperes was supplied from a "VARIAC" brand power supply. A microprocessor based timer was used to control the supply of current for short pulse duration of 0.8–1.2 seconds.

A Hewlett Packard gas chromatograph (Model 5890 Series II) equipped with a flame ionization detector (FID) was used. A 30 m long, 0.32 mm I.D. DB-624 column with 1.8 $\mu$m thick stationary phase (J and W Scientific. Folson, Calif., USA) was used to separate the analytes. All chemicals used in this research were chromatographic grade.

Results and Discussion

Figure 3:
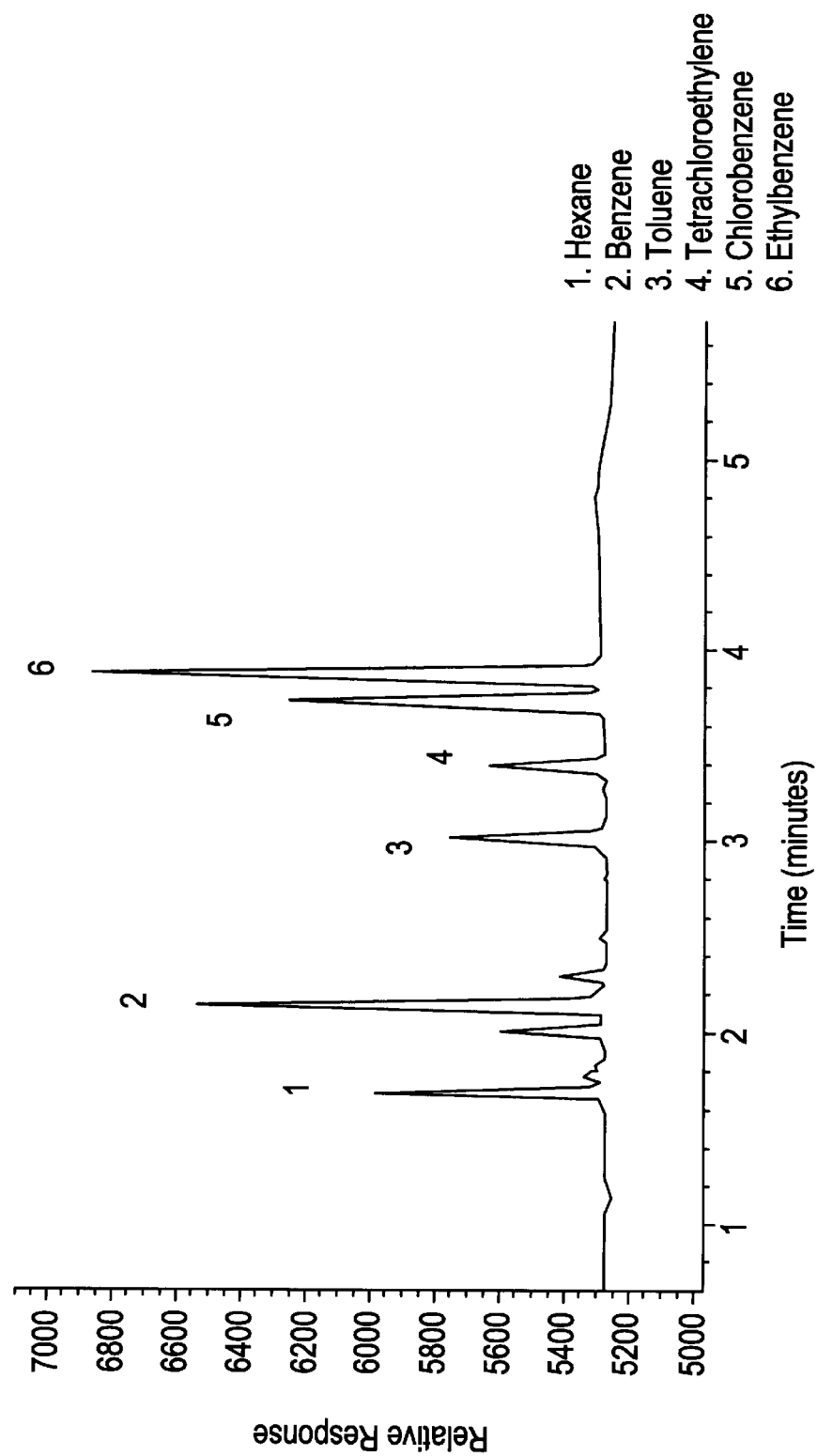
FIG. 3 is a chromatogram of water sample containing different VOCs. The column temperature was held at 50° C. for a minute and then programmed to 105° C. at 20° C. per minute.

Features of the present invention enable one of ordinary skill in the art to obtain accurate results more quickly than can be obtained using heretofore known apparatuses and methods for separating and analyzing at least one component, such as an organic, from an aqueous solution. One such feature involves the introduction of the fluid sample as an injection pulse into the apparatus rather than in a continuous stream fluid sample passing through the feed chamber, which has reported before[10-13]. In particular, the present invention utilizes a first carrier fluid to transport the pulse of fluid sample to the membrane module. In contrast, previous studies taught flowing the fluid sample continuously through the membrane. An example of water determination using the present invention is presented in FIG. 3.

Another feature of the present invention is the utilization of a purge fluid, which is substantially inert. This purge fluid substituted for the first carrier fluid, or mixed with the first carrier fluid, and flowed into the feed chamber after the pulse of fluid sample had passed through the feed chamber. Once in the feed chamber, the purge fluid disrupts the boundary layer which develops over the membrane in the feed chamber, and purges any organics from the membrane. Hence, it speeds up the permeation process, and reduces lat time with minimal loss in sensitivity.

In the description of the invention set forth above, a spiked water sample containing several different organics was analyzed. The concentrations of the organics were at the ppb levels. It is seen that a variety of polar, nonpolar and chlorinated compounds can be analyzed using this technique. The reproducibility or precision was high in terms of retention time as well as peak area used for quantization. The relative standard deviation in peak area based on seven replicate measurements was less than 2% for benzene, toluene, trichloroethane.

The method detection limit (MDL) of selected compounds are listed in Table 1. The detection limit was calculated based on procedure published by the United States Environmental Protection Agency (EPA)[15]. It is clear that detection limits obtained with the apparatus and method of the invention were quite low, at sub parts per billion levels, and more importantly, were lower than those suggested by standard EPA Methods that use purge and trap.

TABLE 1

METHOD DETECTION LIMIT FOR DIFFERENT VOCs

| | MDL OF the present invention (PPB) | SUGGESTED MDL, EPA METHOD 8260 $\mu$g/L(PPB) | SUGGESTED MDL, EPA METHOD 524.2 $\mu$g/L(PPB) |
|---|---|---|---|
| Benzene | 0.0012 | 0.04 | 0.11 |
| Toluene | 0.0063 | 0.11 | 0.11 |
| Ethyl benzene | 0.0450 | 0.06 | 0.06 |
| 1,1,1-Tri-chloroethane | 0.010 | 0.08 | 0.08 |

The apparatus of the Invention can achieve method detectable levels (MDL) significantly lower than the MDL obtained using standard EPA methods, and are comparable to levels achieved using standard purge and trap methods. The detection limits presented here can be further lowered by injecting a larger volume or using a membrane module with larger surface area.

Figure 4:
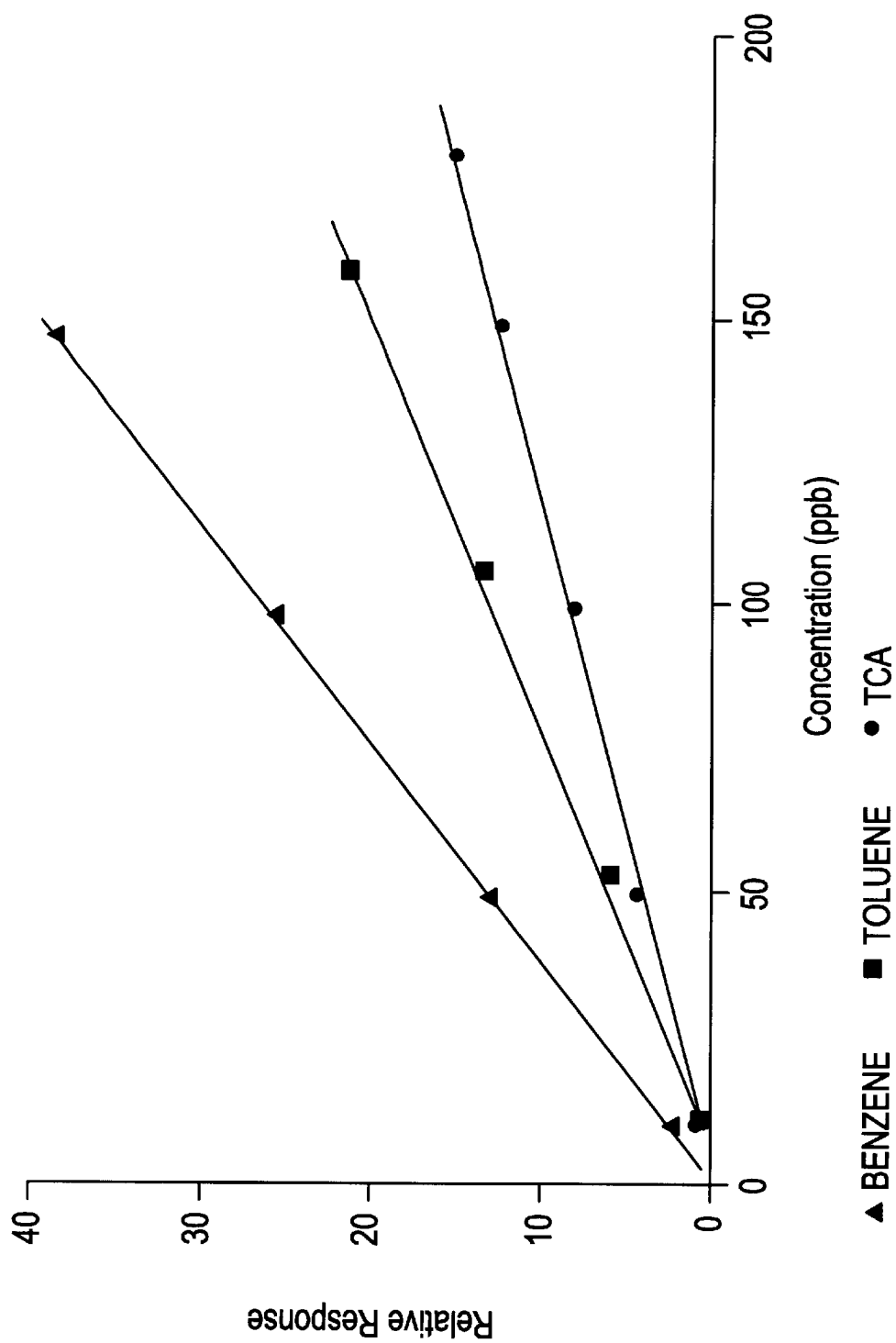
FIG. 4 is a graph of calibration curves generated by the apparatus of the invention.

Moreover, the response obtained using PIME was also proportional to fluid sample concentration. Linear calibration curves were obtained. Calibration curve for benzene, toluene and trichloroethane is shown in FIG. 4. Linearity is attributed to the fact that the extraction efficiency was not a function of concentration. Diffusion coefficient in a membrane is known to vary with concentration especially at high concentrations. However, at these low levels, the diffusion coefficient is constant, resulting in linear calibration curves.

Figure 5:
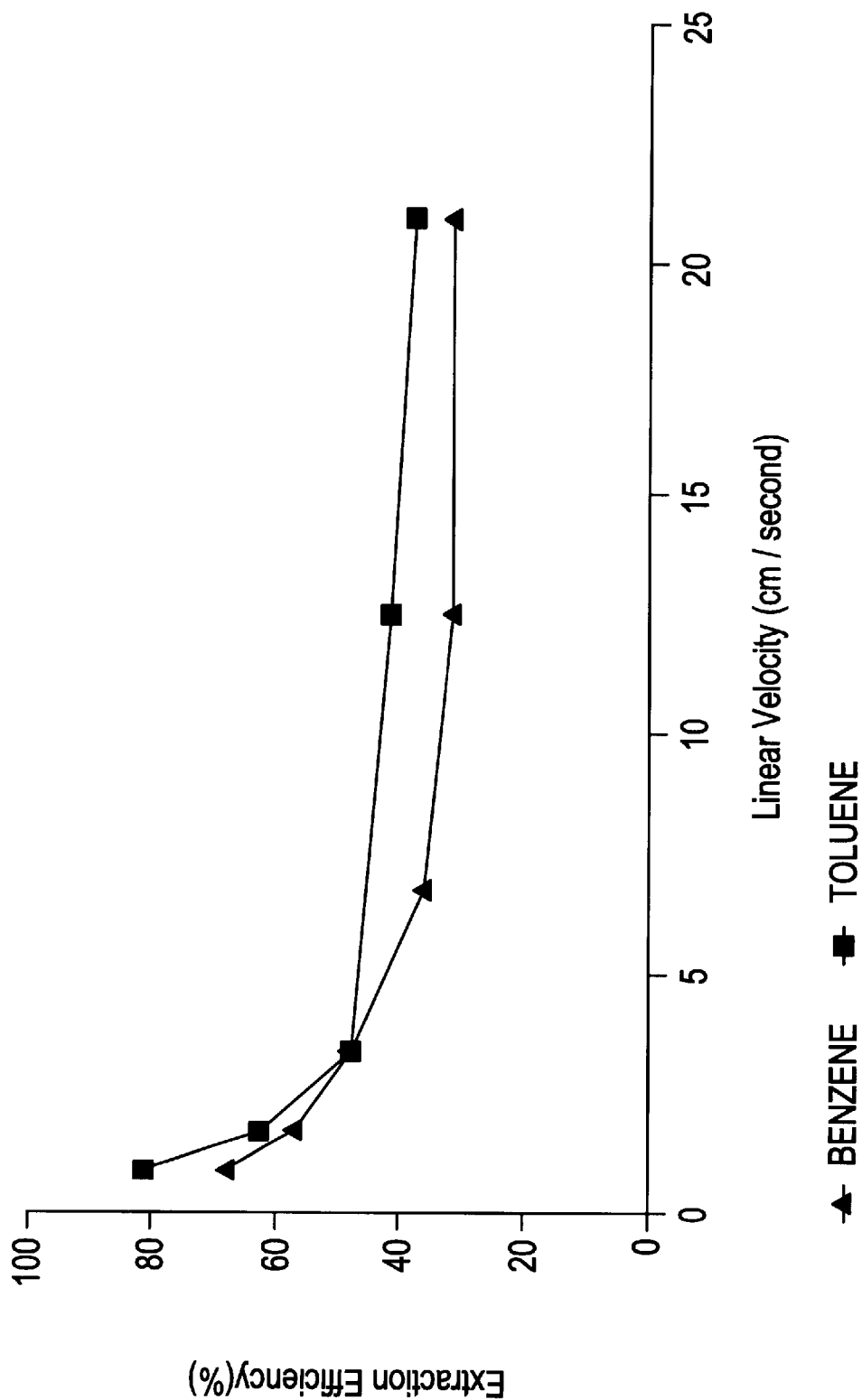
FIG. 5 is a graph of the extraction efficiency of the apparatus of the invention as a function of linear velocity through the membrane.

The permeation through a membrane depends upon several factors such as mass transfer resistance, diffusion coefficient, etc. These factors, in turn, are influenced by operating conditions such as the linear velocity through the membrane, the injection volume and temperature of the membrane module. FIG. 5 shows the variation in extraction efficiency of toluene and benzene as a function of flow rate or linear velocity of the carrier fluid (or the fluid sample) in the membrane module. At high flow rate, the time for which a molecule is in contact with the membrane (or residence time) decreases, consequently there is less time for transfer of the molecules across the boundary layers and through the membrane. As can be seen here, extraction efficiency as high as 80% was achieved at low flow rates. Furthermore, since a pulse of fluid sample is used in the present invention, the volume of the fluid sample can be controlled, and the flow rate can be further lowered to obtain near-quantitative extraction.

Reducing the Lag Time Using a Purge Gas

Figure 6:
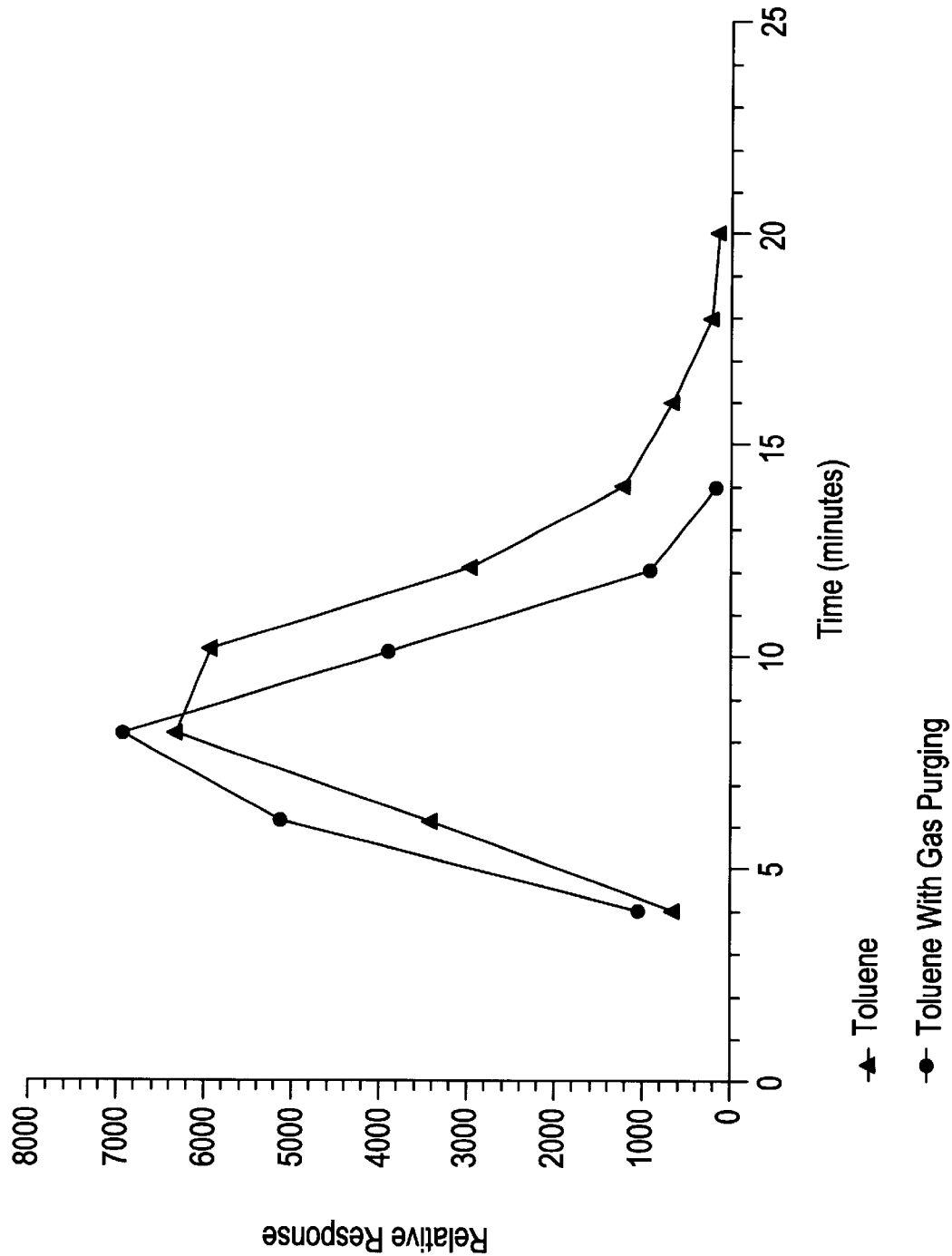
FIG. 6 is a graph which indicates a reduction in lag time using $N_2$ purge gas pursuant to the teaching of the present invention.

One of the problems of traditional membrane extraction methods is that the response time, or lag time, can be fairly long. Initially, a steady state of organics crossing the membrane must be established in order to obtain accurate readings. Setting up such a steady state requires large amounts of fluid sample, and some time for the permeation of the organics through the membrane to equilibrate. It is also time consuming for the organics to cross the boundary layer which develops on the surface of the membrane in traditional pervaporation techniques. In the present invention, a purge fluid is flowed into the feed chamber after the pulse of fluid sample has passed through the feed chamber. The purge fluid disrupts the boundary layer and purges any organics from the membrane, thus reducing the overall response time of the apparatus of the invention. The response time of the apparatus of the invention was measured by injecting toluene and monitoring the GC output as a function of time. The concentration profile is shown in FIG. 6. In a method wherein the fluid sample was flowed continuously through the feed chamber, and no purge fluid was used, it took nearly 16 min for the response to come back to the base line level. To study the effect of the purge gas on response time, after the pulse of fluid sample was injected, a 6 min delay was provided. Then $N_2$ purge gas was permitted to enter the feed chamber. The concentration profile using substantially inert purge fluid is shown in FIG. 6. The data in FIG. 6 clearly indicate that the use of a substantially inert purge fluid as set forth in the present invention resulted in a significant decrease in response time.

Moreover, the apparatus of the present invention has applications in the continuous monitoring of a water stream by injecting a series of discreet fluid samples from a flowing water stream. For each pulse of fluid sample, a microtrap injection is made to obtain the chromatogram. The frequency of analysis would mainly be determined by the time required for GC separation.

CONCLUSION

A pulse introduction membrane extraction apparatus of the invention clearly has applications in separating and analyzing organics in an aqueous fluid sample. It has detection limits in the sub parts per billion levels that are comparable to a purge and trap system. It also has excellent precision and produces a linear calibration curve. A major advantage of this technique is that it can be used for analyzing individual fluid samples of discreet volume as well as for continuous monitoring of a water stream by analyzing a series of fluid samples from a flowing stream.

REFERENCES

1. W. S. Winston Ho and K. K. Sirkar, *Membrane Handbook*, Van Nostrand Reinhold, New York (1992).
2. W. Ji; S. K. Sikdar; and Sun-Tak Hwang, *J. of Membrane Sci.*, 93:1 (1994).
3. S. A. Stern, *J. of Membrane Sci.*, 94: 1 (1994).
4. S. Bauer and D. Solyom, *Anal. Chem.*, 66:4422 (1994).
5. M. A. Lapack and J. C. You, *Anal. Chem.*, 63, 1631 (1991).
6. T. Kotiaho; F. r. Lauritsen; T. K. Chpudhury; R. G. Cooks; and G. T. Tsao, *Anal. Chem.*, 63(18):875A (1991).
7. L. E. Silivon; M. R. Bauer; A. S. Ho; and W. L. Budde, *Anal. Chem.*, 63:1335 (1991).
8. S. Mitra; L. Zhang; N. Zhu; and x. Guo, *Journal of Micro Column Separation*, 8(1):21 (1996).
9. S. Mitra; N. Zhu; X. Zhang; and B. Kebbekus, *Journal of Chromatography A*, 736:165–173 (1996).
10. S. Mitra, *Continuous Monitoring of Organic Pollutants*, U.S. Pat. No. 5,435,169, 1995.
11. Y. Xu and S. Mitra, *Journal of Chromatography*, 688:171 (1994).
12. S. Mitra, *Instrumentation for VOCs Monitoring*, Patent Pending (1996).
13. S. Mitra; Y. Xu; W. Chen and a. Lai, *Journal of Chromatography A*, 727:111–118 (1996).
14. S. Mitra and C. Yun, *Journal of Chromatography*, 684:415 (1993).
15. Code of Federal Register, 49, Part 136, Appendix B.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

Various publications are cited herein, the disclosures of which are incorporated by reference in their entireties.

What is claimed is:

1. An apparatus for the continuous on-line or discrete individual separation and analysis of at least one component of a fluid sample, the apparatus comprising:

a feed chamber having an entrance and an exit;

a first flow means upstream of said feed chamber for flowing a first carrier fluid through said feed chamber;

pulse injection means for injecting a pulse of fluid sample containing at least one component into said first carrier fluid, said first carrier fluid being different from said sample and said component, such that said pulse of fluid sample enters said feed chamber in said carrier fluid;

an exit chamber downstream from said feed chamber;

at least one membrane through which said at least one component can selectively permeate, wherein said at least one membrane is located between said feed chamber and said exit chamber and in fluid registry therewith;

a detector in fluid communication with said exit chamber, wherein said detector is operative to analyze said at least one component that passes through said membrane and enters said exit chamber; and a second flow means for flowing said at least one component which passes through said at least one membrane and enters said exit chamber, to said detector.

2. The apparatus of claim 1, wherein said fluid sample comprises an aqueous solution, said at least one component comprises an organic, and said first carrier fluid is selected from the group consisting of water, water with salt or other additives, organic solvents, nitrogen, carbon dioxide, argon, neon, other inert gases, and a combination thereof.

3. The apparatus of claim 1, wherein said first flow means comprises a first reservoir of said first carrier fluid upstream from said feed chamber and in fluid communication therewith, and a pump in fluid communication with said first reservoir, such that said first carrier fluid is pumped through said feed chamber.

4. The apparatus of claim 3, wherein said means for injecting said pulse of fluid sample into said feed chamber comprises a multi-port valve upstream from said feed chamber and downstream from said first reservoir, wherein said multi-port valve is in fluid communication with said first reservoir and said feed chamber, and comprises a first port through which said pulse of fluid sample is injected into said flow of said first carrier fluid.

5. The apparatus of claim 1, further comprising a means for flowing a substantially inert purge fluid into said feed chamber after said pulse of fluid sample has passed through said feed chamber.

6. The apparatus of claim 5, wherein said means for flowing said purge fluid comprises a switching valve upstream from said multi-port valve and downstream from said first reservoir, and in fluid communication with said first reservoir and said multi-port valve, and a second reservoir for holding said substantially inert purge fluid in fluid communication with said switching valve, such that operation of said switching valve prevents said first carrier fluid from entering said feed chamber after said pulse of fluid sample has passed through said feed chamber, and permits said substantially inert purge fluid to flow from said second reservoir into said feed chamber after said pulse of fluid sample has passed through said feed chamber.

7. The apparatus of claim 6, wherein said substantially inert fluid is selected from the group consisting of $N_2$, $CO_2$, neon and helium.

8. The apparatus of claim 1, wherein said at least one membrane is symmetrical in structure.

9. The apparatus of claim 1, wherein said at least one membrane is asymmetrical in structure.

10. The apparatus of claim 1, wherein said at least one membrane comprises at least one hollow fiber having a bore and an outer surface, and said at least one hollow fiber is contained within a shell, such that said bore defines said feed chamber, and said shell and said outer surface of said hollow fiber define said exit chamber.

11. The apparatus of claim 10, wherein said bore has a diameter of about 0.305 mm, and said at least one hollow fiber has an outer diameter of 0.635 mm.

12. The apparatus of claim 1, wherein said membrane comprises nonporous hydrophobic material.

13. The apparatus of claim 12, wherein said nonporous hydrophobic material is selected from the group consisting of polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, and polyethers.

14. The apparatus of claim 13, wherein said at least one membrane is comprised of polydimethylsiloxane.

15. The apparatus of claim 1, wherein said at least one membrane is a membrane composite comprising a porous membrane having a first and second surface, and a nonporous hydrophobic membrane permanently disposed on said second surface of the porous membrane, such that said first surface of said porous membrane is in fluid registry with said exit chamber, and said nonporous hydrophobic membrane is in fluid registry with said feed chamber.

16. The apparatus of claim 15, wherein said porous membrane is selected from the group consisting of polypropylene, polyethylene, polytrimethylpentene, polytetrafluoroethylene, polyvinylidene difluoride, and polysulfone.

17. The apparatus of claim 15, where said porous membrane has pores that range in size from about 6 to about 500 Å.

18. The apparatus of claim 15, wherein said nonporous hydrophobic membrane is selected from the group consisting of polydimethylsiloxane (silicone rubber), nitrile rubber, neoprene rubber, silicone-polycarbonate copolymers, fluoroelastomers, polyurethane, polyvinylchloride, polybutadiene, polyolefin elastomers, polyesters, and polyethers.

19. The apparatus of claim 1, further comprising an injecting means for injecting said at least one component which passes through said at least one membrane and enters said exit chamber, into said detector, wherein said injecting means is located downstream from said exit chamber, and upstream from said detector, and in fluid communication with said exit chamber and said detector.

20. The apparatus of claim 19, wherein the injection means comprises a trap means comprising a column having a first end in fluid communication with said exit chamber, and a second end in fluid communication with said detector, wherein said column is packed with a packing material to which said at least one component can reversibly adsorb, and a releasing means which desorbs said at least one component from said packing material.

21. The apparatus of claim 20, wherein said column is prepared from a material selected from the group consisting of stainless steel, "TEFLON", polypropylene, and glass.

22. The apparatus of claim 20, wherein the packing material is selected from the group consisting of "TENAX", silica gel, and a carbon based sorbent.

23. The apparatus of claim 22, wherein the carbon based sorbent is selected from the group consisting of charcoal, "CARBOTRAP C", "CARBOSIEVE", "CARBOPACK" and a combination thereof.

24. The apparatus of claim 20, wherein said at least one component is an organic, and said column comprises a length of 15 cm, an outer diameter of 0.53 mm, and is comprised of stainless steel, and is packed with "CARBOTRAP C".

25. The apparatus of claim 20, wherein said releasing means comprises a means for heating said packing material such that said organic can desorb from said packing material.

26. The apparatus of claim 25, wherein said column comprises stainless steel, and said heating means comprises a power supply electrically connected to said column, such that an electric current can be applied to said column, which then undergoes resistive heating and heats said packing material.

27. The apparatus of claim 1, wherein said detector is selected from the group consisting of a gas chromatograph, a high performance liquid chromatograph, a gas chromatograph coupled to a mass spectrometer, a capillary electrophoresis instrument, a mass spectrometer, a total organic carbon analyzer, an infra red (IR) spectrometer, an ultraviolet (UV) spectrometer, a Raman spectrometer, and a fluorescence spectrometer.

28. The apparatus of claim 1, wherein said second flow means comprises a third reservoir holding a second carrier fluid, wherein said second reservoir is in fluid communication with said exit chamber, such that said second carrier fluid flows from said second reservoir through said exit chamber, to said detector.

29. The apparatus of claim 28, wherein said second carrier fluid comprises nitrogen, hydrogen or helium.

30. A process for the continuous on-line or discrete individual separation and analysis of at least one component of a fluid sample, practiced with an apparatus comprising:
    a feed chamber having an entrance and an exit;
    a first flow means upstream of said feed chamber for flowing a first carrier fluid through said feed chamber;
    pulse injection means for injecting a pulse of fluid sample containing at least one component into said first carrier fluid, said first carrier fluid being different from said sample and said component, such that said pulse of fluid sample enters said feed chamber in said carrier fluid; an exit chamber downstream from said feed chamber;

at least one membrane through which said at least one component can selectively permeate, wherein said at least one membrane is located between said feed chamber and said exit chamber and in fluid registry therewith;

a detector in fluid communication with said exit chamber, wherein said detector is operative to analyze said at least component that passes through said membrane and enters said exit chamber; and a second flow means for flowing said at least one component which passes through said at least one membrane and enters said exit chamber, to said detector, the process comprising the steps of:
- a) flowing the first carrier fluid through the feed chamber;
- b) injecting the pulse of fluid sample into the first carrier so that the pulse of fluid sample enters the feed chamber;
- c) passing said pulse of fluid sample to said exit chamber;
- d) passing said pulse of fluid sample from said exit chamber to said detector; and
- e) detecting the at least one component.

31. The process of claim 30, wherein said apparatus includes a concentration device located in fluid registry between said exit chamber and said detector, and said pulse of fluid sample is concentrated in said concentration device after passing through said exit chamber and before entering said detector.

32. The process of claim 31, wherein said concentration device is selected from the group consisting of a sorbent trap, a cryogenic trap, a gas sample valve, and combinations thereof.

33. The process of claim 30, wherein the fluid sample comprises an aqueous solution, and the first carrier fluid is selected from the group consisting of water, water with salt or other additives, organic solvents, nitrogen, carbon dioxide, argon, neon, other inert gases, and a combination thereof.

34. The process of claim 30, wherein the step of flowing the first carrier fluid through the feed chamber comprises providing a first reservoir which holds the first carrier fluid upstream from the feed chamber, and providing a pump in fluid communication with the first reservoir, such that the first carrier fluid is pumped through the feed chamber.

35. The process of claim 34, wherein the step of injecting the pulse of fluid sample into the feed chamber comprises providing a multi-port valve upstream from the feed chamber and downstream from the first reservoir, wherein the multi-port valve is in fluid communication with the first reservoir and the feed chamber, and comprises a first port through which the pulse of fluid sample is injected into the flow of the first carrier fluid.

36. The process of claim 35, further comprising the step of flowing a substantially inert purge fluid into the feed chamber after the pulse of fluid sample has entered the feed chamber.

37. The process of claim 36, wherein the step of flowing the substantially inert purge fluid into the feed chamber comprises providing a switching valve upstream from the multi-port valve and downstream from the first reservoir, and in fluid communication with the first reservoir and the multi-port valve, providing a second reservoir for holding the substantially inert purge fluid in fluid communication with the switching valve, and operating the switching valve such that the first carrier fluid is prevented from entering the feed chamber after the pulse of fluid sample has passed through the feed chamber, and the substantially inert purge fluid is permitted to flow from the second reservoir into the feed chamber after the pulse of fluid sample has passed through the feed chamber.

38. The process of claim 36, wherein the substantially inert purge fluid is selected from the group consisting of $N_2$, $CO_2$, neon and helium.

39. The process of claim 30, wherein the at least one component comprises an organic, and the injecting step comprises the steps of providing a trap means comprising a column having a first end in fluid communication with the exit chamber, and a second end in fluid communication with the detector, wherein the column is packed with a packing material to which the organic can reversibly adsorb, and providing a releasing means for releasing the at least one component trapped in the trap means.

40. The process of claim 39, wherein the column is prepared from a material selected from the group consisting of stainless steel, "TEFLON", polypropylene, and glass.

41. The process of claim 40, wherein the packing material is selected from the group consisting of "TENAX", silica gel, and a carbon based sorbent.

42. The process of claim 41, wherein the carbon based sorbent is selected from the group consisting of charcoal, "CARBOTRAP C", "CARBOSIEVE", "CARBOPACK", and a combination thereof.

43. The process of claim 39, wherein the column comprises a length of about 15 cm, an outer diameter of about 0.53 mm, is comprised of stainless steel, and is packed with "CARBOTRAP C".

44. The process of claim 39, wherein the releasing means comprises a power supply electrically connected to the column, such that an electric current is applied to the column, which undergoes resistive heating and heats the packing material.

45. The process of claim 30, wherein the step of detecting the at least one component comprises providing a detector.

46. The process of claim 45, wherein the detector is selected from the group consisting of a gas chromatograph, a high performance liquid chromatograph, a gas chromatograph coupled to a mass spectrometer, a capillary electrophoresis instrument, a mass spectrometer, a total organic carbon analyzer, an infra red (IR) spectrometer, an ultraviolet (UV) spectrometer, a Raman spectrometer, and a fluorescence spectrometer.

47. The process of claim 30, wherein the second flow means comprises a third reservoir for holding a second carrier fluid under pressure, wherein the third reservoir is in fluid communication with the exit chamber, such that the second carrier fluid flows from the third reservoir, through the exit chamber to the detector.

48. The process of claim 47, wherein the second carrier fluid is selected from the group consisting of nitrogen, hydrogen, and helium.

* * * * *